(12) United States Patent
Oshida

(10) Patent No.: US 8,872,304 B2
(45) Date of Patent: Oct. 28, 2014

(54) SEMICONDUCTOR DEVICE AND METHOD OF MANUFACTURING THE SAME

(71) Applicant: Renesas Electronics Corporation, Kawasaki (JP)

(72) Inventor: Daisuke Oshida, Kanagawa (JP)

(73) Assignee: Renesas Electronics Corporation, Kanagawa (JP)

( * ) Notice: Subject to any disclaimer, the term of this patent is extended or adjusted under 35 U.S.C. 154(b) by 0 days.

(21) Appl. No.: 13/754,014

(22) Filed: Jan. 30, 2013

(65) Prior Publication Data

US 2013/0207269 A1 Aug. 15, 2013

(30) Foreign Application Priority Data

Feb. 10, 2012 (JP) ................. 2012-026990

(51) Int. Cl.

| | |
|---|---|
| *H01L 21/70* | (2006.01) |
| *H01L 21/02* | (2006.01) |
| *H01L 23/488* | (2006.01) |
| *H01L 21/311* | (2006.01) |
| *H01L 23/522* | (2006.01) |
| *H01L 23/532* | (2006.01) |
| *H01L 21/768* | (2006.01) |

(52) U.S. Cl.
CPC ........ *H01L 23/488* (2013.01); *H01L 21/02697* (2013.01); *H01L 21/31116* (2013.01); *H01L 21/31144* (2013.01); *H01L 23/5222* (2013.01); *H01L 23/53295* (2013.01); *H01L 21/7682* (2013.01); *H01L 2924/0002* (2013.01)
USPC .................. 257/522; 257/410; 257/E21.573; 257/E21.581

(58) Field of Classification Search
USPC .......... 257/522, 734, E21.573, 758, 762, 760, 257/763, 764; 438/622
See application file for complete search history.

(56) References Cited

U.S. PATENT DOCUMENTS

| | | | | |
|---|---|---|---|---|
| 6,917,109 | B2 * | 7/2005 | Lur et al. ....................... | 257/758 |
| 7,553,756 | B2 * | 6/2009 | Hayashi et al. ............... | 438/622 |
| 2007/0246831 | A1 * | 10/2007 | Gabric et al. ................. | 257/758 |
| 2008/0042268 | A1 * | 2/2008 | Yu et al. ......................... | 257/734 |
| 2009/0072410 | A1 * | 3/2009 | Clevenger et al. ............ | 257/774 |

FOREIGN PATENT DOCUMENTS

JP 2007-141985 A 6/2007

\* cited by examiner

*Primary Examiner* — Cuong Q Nguyen
*Assistant Examiner* — Nishath Yasmeen
(74) *Attorney, Agent, or Firm* — Foley & Lardner LLP

(57) ABSTRACT

A semiconductor device in which misalignment does not cause short-circuiting and inter-wiring capacitance is decreased. Plural wirings are provided in a first interlayer insulating layer. An air gap is made between at least one pair of wirings in the layer. A second interlayer insulating layer lies over the wirings and first interlayer insulating layer. The first bottom face of the second interlayer insulating layer is exposed to the air gap. When a pair of adjacent wirings whose distance is shortest are first wirings, the upper ends of the first interlayer insulating layer between the first wirings are in contact with the first wirings' side faces. The first bottom face is below the first wirings' upper faces. $b/a \leq 0.5$ holds where a represents the distance between the first wirings and b represents the width of the portion of the first interlayer insulating layer in contact with the first bottom face.

19 Claims, 16 Drawing Sheets

SEMICONDUCTOR DEVICE AND METHOD OF MANUFACTURING THE SAME

CROSS-REFERENCE TO RELATED APPLICATIONS

The disclosure of Japanese Patent Application No. 2012-026990 filed on Feb. 10, 2012 including the specification, drawings and abstract is incorporated herein by reference in its entirety.

BACKGROUND

The present invention relates to a semiconductor device and a method of manufacturing the same.

In recent years, a semiconductor device with an air gap in a multilayer wiring layer has been proposed.

Japanese Unexamined Patent Publication No. 2007-141985describes a method of manufacturing a semiconductor device as follows. First, a sacrificial film pillar as a selectively removable insulating film is formed in a region for the formation of a via. Then, an interlayer insulating layer is formed between adjacent wirings. At this time, an air gap is made in the interlayer insulating layer. This structure is claimed to separate the via from the air gap completely.

SUMMARY

However, there is a possibility that the above related art cannot decrease inter-wiring capacitance to a desired level. The present inventors have found a problem that misalignment of a via over a wiring makes it difficult to both prevent short-circuiting and decrease inter-wiring capacitance.

According to one aspect of the present invention, there is provided a semiconductor device which includes a first interlayer insulating layer, a plurality of wirings provided in the first interlayer insulating layer, an air gap made between at least one pair of the wirings in the first interlayer insulating layer, and a second interlayer insulating layer provided over the wirings and the first interlayer insulating layer with a first bottom face thereof exposed to the air gap. When the pair of adjacent wirings whose distance is shortest are first wirings, the upper ends of the first interlayer insulating layer lying between the first wirings are in contact with side faces of the first wirings, the first bottom face is below the upper faces of the first wirings, and $b/a \leq 0.5$ holds where a represents distance between the first wirings and b represents width of a portion of the first interlayer insulating layer which is in contact with the first bottom face.

According to another aspect of the invention, there is provided a method of manufacturing a semiconductor device which includes the following steps: forming a first interlayer insulating layer over a semiconductor substrate, making a plurality of wiring gutters in the first interlayer insulating layer and burying metal in the wiring gutters to form a plurality of wirings (wiring formation step), etching back the first interlayer insulating layer using the wirings as a mask to form, between at least one pair of the wirings in the first interlayer insulating layer, a first trench having first side faces in contact with the wirings and a bottom face between the first side faces (first trench formation step), anisotropically etching at least the bottom face of the first trench selectively to form a second trench in the first interlayer insulating layer (second trench formation step), and forming a second interlayer insulating layer over the wirings and the first interlayer insulating layer and making an air gap between at least one pair of the wirings in the first interlayer insulating layer by infilling an upper portion of the second trench.

According to the present invention, the upper ends of the first interlayer insulating layer between adjacent first wirings whose distance is shortest are in contact with the side faces of the first wirings. The first bottom face is below the upper faces of the first wirings. When the distance between the first wirings is expressed as a and the distance of the portion of the first interlayer insulating layer which is in contact with the first bottom face is expressed as b, the ratio of b to a is a prescribed ratio. Consequently, a misaligned via is formed in the second interlayer insulating layer in contact with the first wirings. Thus, the misaligned via and wirings are not short-circuited through the air gap. Therefore, in the semiconductor device, misalignment does not cause short-circuiting and decreases inter-wiring capacitance.

According to the present invention, it is possible to provide a semiconductor device in which misalignment does not cause short-circuiting and inter-wiring capacitance is decreased.

BRIEF DESCRIPTION OF THE DRAWINGS

FIGS. 3A and 3B are enlarged plan views of the semiconductor device according to the first embodiment, in which FIG. 3A shows linear wirings and FIG. 3B shows bent wirings;

FIGS. 8A and 8B are sectional views illustrating the method of manufacturing a semiconductor device according to the first embodiment, in which FIG. 8A shows a lower interlayer insulating layer and FIG. 8B shows a first interlayer insulating layer over it;

FIGS. 9A and 9B are sectional views illustrating the method of manufacturing a semiconductor device according to the first embodiment, in which FIG. 9A shows the formation of wirings and FIG. 9B shows the formation of cap layers;

FIGS. 10A and 10B are sectional views illustrating the method of manufacturing a semiconductor device according to the first embodiment, in which FIG. 10A shows the formation of a first trench and FIG. 10B shows the formation of a second trench;

FIGS. 11A and 11B are sectional views illustrating the method of manufacturing a semiconductor device according to the first embodiment, in which FIG. 11A shows the formation of an air gap and FIG. 11B shows the formation of a via;

FIGS. 12A and 12B illustrate the advantageous effect of the first embodiment, in which FIG. 12A shows a comparative example and FIG. 12B shows the first embodiment;

DETAILED DESCRIPTION

Figure 1:
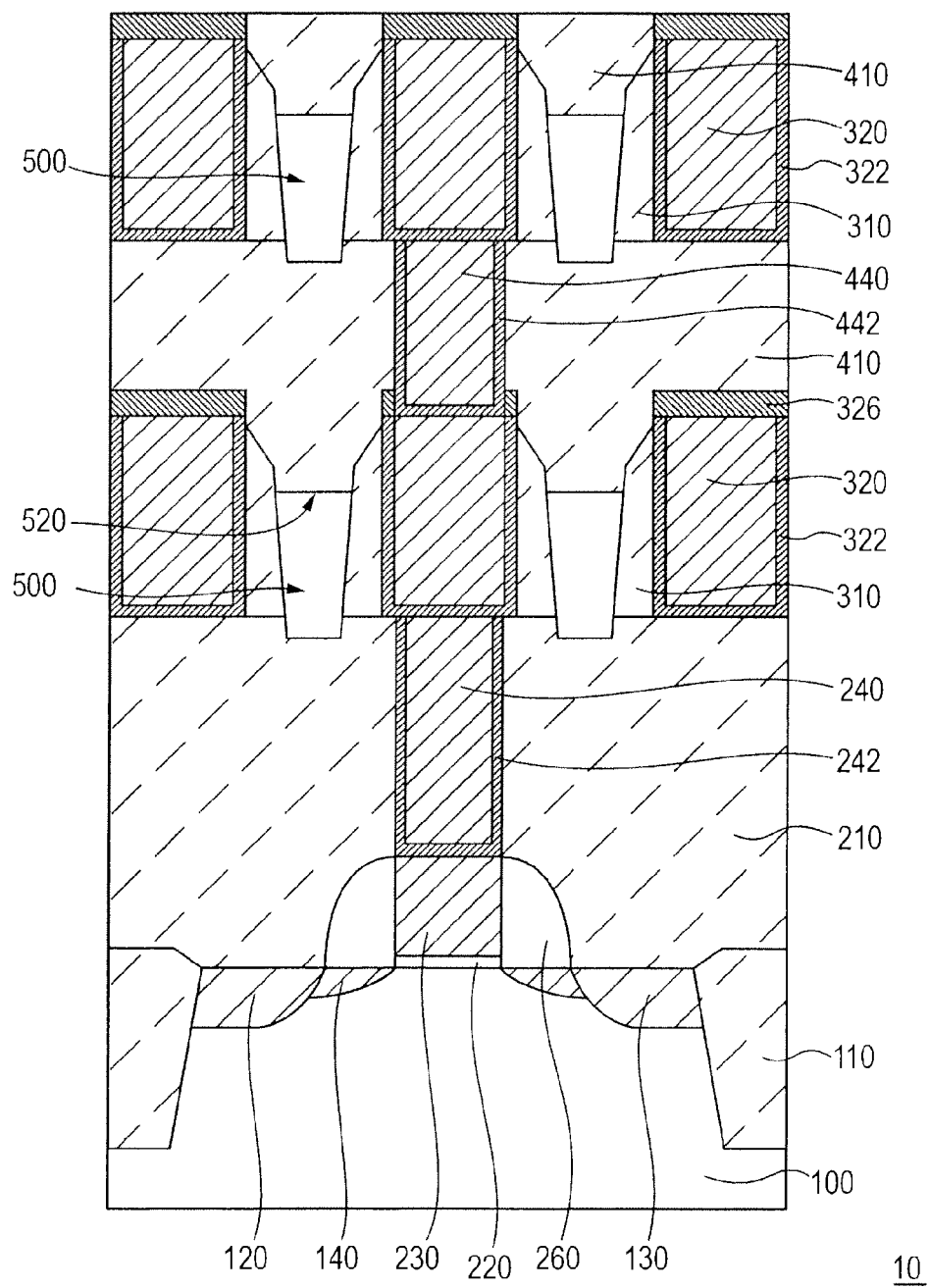
FIG. 1 is a sectional view showing the structure of a semiconductor device according to a first embodiment of the invention.

Next, the preferred embodiments of the present invention will be described referring to the accompanying drawings. In all the drawings, the same elements are designated by the same reference numerals and repeated descriptions of the same elements are omitted as appropriate.

First Embodiment

Next, a semiconductor device 10 according to the first embodiment will be described referring to FIGS. 1 to 6. The semiconductor device 10 has the following structure. A plurality of wirings 320 are provided in a first interlayer insulating layer 310. An air gap 500 is provided between at least one pair of wirings 320 in the first interlayer insulating layer 310. A second interlayer insulating layer 410 is provided over the wirings 320 and first interlayer insulating layer 310. The first bottom face 520 of the second interlayer insulating layer 410 is exposed to the air gap 500. When a pair of adjacent wirings 320 whose distance is shortest are referred to as first wirings, the upper ends of the first interlayer insulating layer 310 between the first wirings are in contact with the side faces of the first wirings. The first bottom face 520 is located below the upper faces of the first wirings. The relation of b/a≤0.5 holds where a represents the distance between the first wirings and b represents the width of the portion of the first interlayer insulating layer 310 which is in contact with the first bottom face 520. Details are given below.

First, the overall structure of the semiconductor device will be described referring to FIG. 1. FIG. 1 is a sectional view showing the structure of the semiconductor device 10 according to the first embodiment.

The semiconductor substrate 100 is, for example, a Si substrate. In the explanation give below, a constituent element of the semiconductor device 10 is described as being "located below" A, it means that the element is located nearer to the semiconductor substrate 100 than A. The semiconductor substrate 100 includes an element isolation region 110 having an opening (not designated by a reference numeral in the figure). The element isolation region 110, which is, for example, an insulating film of $SiO_2$, is formed by a LOCOS (Local Oxidation of Silicon) process. Alternatively, the element isolation region 110 may be formed by an STI (Shallow Trench Isolation) process.

A source region 120 and a drain region 130 are provided in the semiconductor substrate 100 in a way to be spaced from each other in a plan view. Extension regions 140 are located between the source region 120 and drain region 130 in a way to be in contact with them respectively.

A gate insulating layer 220 is located between the extension regions 140. A gate electrode 230 is provided over the gate insulating layer 220. Sidewall insulating films 260 are provided on the sidewalls at both sides of the gate insulating layer 220 and gate electrode 230. These elements make up a transistor (MISFET: Metal Insulator Semiconductor Field Effect Transistor) as a semiconductor device.

A lower interlayer insulating layer 210 is provided over the semiconductor substrate 100, element isolation region 110, sidewall insulating films 260 and gate electrode 230. The lower interlayer insulating layer 210 is made, for example, of the same material as the first interlayer insulating layer 310 which will be described later.

The lower interlayer insulating layer 210 has a contact plug 240. A barrier metal layer 242 lies on the bottom face and side faces of the contact plug 240. The contact plug 240 is coupled, for example, to the gate electrode 230. In a plan view, the contact plug 240 is coupled to the source region 120 or drain region 130 in a different region. The contact plug 240 is made, for example, of W. The barrier metal layer 242 is made of Ti, Ta, W or nitride of any of these metals.

An anti-diffusion layer (not shown) may be provided over the lower interlayer insulating layer 210.

A first interlayer insulating layer 310 is provided over the lower interlayer insulating layer 210. This decreases the inter-wiring capacitance of the semiconductor device 10. Specifically the first interlayer insulating layer 310 is, for example, film of $SiO_2$, SiON, SiOC, SiOCH, SiCOH or SiOF. Instead, the first interlayer insulating layer 310 may be HSQ (Hydrogen Silsesquioxane) film, MSQ (Methyl Silsesquioxane) film or other organic polymer. Also, the first interlayer insulating layer 310 may be porous film, MPS (Molecular Pore Stack) film or dense film. Here "MPS film" means film comprised of molecular pores and "dense film" means high-density film.

The first interlayer insulating layer 310 may be insulating film containing low-k film or film which has a low relative dielectric constant (for example, 3.2 or less). This contributes to decreasing the inter-wiring capacitance in the overlying and underlying layers and the same layer. It is particularly useful in the sixth embodiment which will be described later, because the inter-wiring capacitance in a region with no air gap 500 is decreased.

The first interlayer insulating layer 310 includes a plurality of wirings 320. A barrier metal layer 322 lies on the bottom face and side faces of each wiring 320. For example, the wiring 320 contains Cu. The barrier metal layer 322 is, for example, made of Ti, Ta, W, Ru or nitride of any of these metals or a laminate of any combination of these metals.

The wiring 320 is coupled, for example, to the contact plug 240. Specifically, the wiring 320 is formed in a way to overlap the contact plug 240 in a plan view. The wiring 320 is coupled, for example, through the contact plug 240 to the gate electrode 230. The wiring 320 is coupled, for example, through the contact plug 240 to the source region 120 or drain region 130 in a region which is not shown in the figure.

A cap layer may lie over the wiring 320. The cap layer is located in a way to overlap the wiring 320 in a plan view. The cap layer is made of at least a material different from the first interlayer insulating layer 310. Here, the "cap layer" functions as a mask over the wiring 320 in the first trench formation step and second trench formation step which will be described later. The "cap layer" has a function to prevent diffusion of copper (Cu). Preferably the "cap layer" is made of a material with a lower etching rate than the material of the first interlayer insulating layer 310 under the conditions for etching the first interlayer insulating layer 310 in the first trench formation step and second trench formation step.

As the cap layer, for example, a metal cap layer 326 is used. The existence of the cap layer makes it possible to make the air gap 500 stably as will be described later. For example, the metal cap layer 326 as the cap layer contains Ta, TaN, Ti, TiN, Mn, CoWP, CoWB, Co, NiB, W, Al or any one of alloys of these metals. This prevents the wiring 320 from being etched in the first trench formation step or second trench formation step. The wiring 320 is formed, for example, by a damascene process.

The metal cap layer 326 is formed, for example, by being selectively grown over the wiring 320 as will be described later. The metal cap layer 326 need not lie over the barrier metal layer 322.

An air gap 500 is provided between at least one pair of wirings 320 in the first interlayer insulating layer 310. Here, "air gap 500" refers to a hole made in the first interlayer insulating layer 310. This can decrease inter-wiring capacitance. The air gap 500 will be described in detail later.

A second interlayer insulating layer 410 is provided over the wirings 320 and the first interlayer insulating layer 310. The first bottom face 520 of the second interlayer insulating layer 410 is exposed to the air gap 500. The second interlayer insulating layer 410 is made, for example, of the same material as the first interlayer insulating layer 310. Alternatively the second interlayer insulating layer 410 may be made of a different material from the first interlayer insulating layer 310. Also, the first interlayer insulating layer 310 and second interlayer insulating layer 410 may be each comprised of more than one insulating layer.

The second interlayer insulating layer 410 has a via 440. A barrier metal layer 442 lies on the bottom face and side faces of the via 440. The lower end of the via 440 is in contact with the upper face of the wiring 320. If a metal cap layer 326 lies over the wiring 320, the via 440 penetrates the metal cap layer 326 and contacts the wiring 320. The via 440 is made of, for example, of the same material as the wiring 320. The barrier metal layer 442 is made of, for example, the same material as the barrier metal layer 322.

Another first interlayer insulating layer 310 may be provided over the second interlayer insulating layer 410. A plurality of wirings 320 are provided in the first interlayer insulating layer 310. The wiring 320 in an upper layer is coupled through the via 440 to the wiring 320 in a lower layer. The first interlayer insulating layer 310 contains an air gap 500. A plurality of wiring layers having the same structure as mentioned above may be stacked one upon another. Also, an anti-diffusion layer (not shown) may be provided between the first interlayer insulating layer 310 and second interlayer insulating layer 410.

For example, bump electrodes (not shown) are provided over the uppermost layer of the above multilayer wiring structure. Over the uppermost layer, electrode pads (not shown) may be provided and bonding wires (not shown) may be coupled there. The semiconductor substrate 100 is mounted, for example, over a wiring board (not shown).

Next, the air gap 500 will be described in detail referring to FIGS. 2 to 6.

Figure 2:
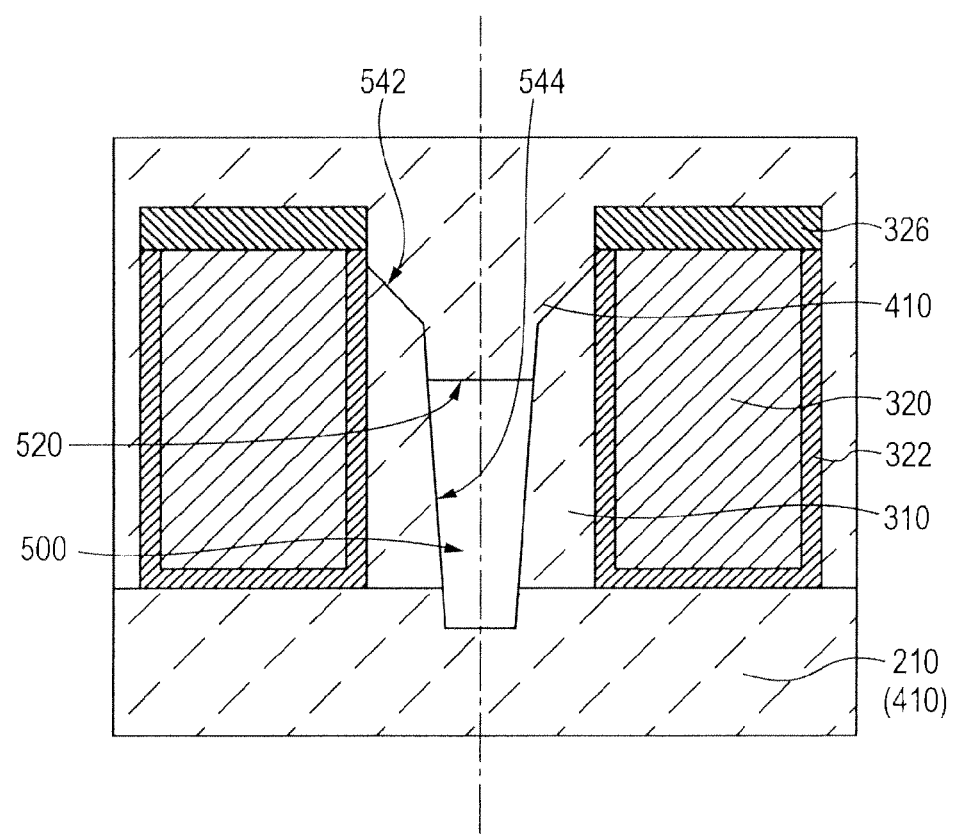
FIG. 2 is an enlarged sectional view of the semiconductor device according to the first embodiment.

FIG. 2 is an enlarged sectional view of the semiconductor device 10 according to the first embodiment. FIG. 2 shows, among the wirings 320, adjacent wirings 320 whose distance is shortest.

As shown in FIG. 2, the upper ends of the first interlayer insulating layer 310 between the first wirings (wirings 320) are in contact with the side faces of the first wirings (wirings 320). The side face of the first interlayer insulating layer 310 which is in contact with each first wiring is referred to as the "first side face 542." The first side face 542 is, for example, a flat surface. Alternatively the first side face 542 may be a curved surface. The side face of the first interlayer insulating layer 310 which is exposed to the air gap 500 and in contact with the bottom face of the air gap 500 is referred to as the "second side face 544." If the bottom face of the air gap 500 lies in an underlying interlayer insulating layer, the second side face 544 includes the underlying interlayer insulating layer. In other words, the "second side face 544" is a side face of a second trench 360 which will be described later.

The upper end of the first interlayer insulating layer 310 which is in contact with each wiring 320 is located below the upper face of the wiring 320. Not only the first wirings but also wirings 320 more spaced from each other than the first wirings may be formed in this way. In the second trench formation step which will be described later, etching is done so that the upper face of the first interlayer insulating layer 310 is below the upper face of the first wiring. In other words, the first interlayer insulating layer 310 between first wirings (wirings 320) is formed like sidewalls of the first wirings (wirings 320) in a self-aligning manner.

The first bottom face 520 of the second interlayer insulating layer 410 is located below the upper faces of the first wirings. This prevents the material contained in the via 440 from diffusing in the air gap 500 even if there is misalignment of the via 440 or the via 440 has a larger diameter than standard due to production tolerance. Therefore, short-circuiting between the wirings 320 can be suppressed. Here, "misalignment" means that the via 440 protrudes outward from a wiring 320 in a plan view.

The first bottom face 520 is, for example, a flat surface. Alternatively the first bottom face 520 may be a curved surface. The first bottom face 520 may be a convex surface protruding toward the air gap 500 or concave surface recessed toward the second interlayer insulating layer 410.

The first bottom face 520 should be located below the lower end of a misaligned via 440 in a sectional view. Consequently the via 440 is never coupled to the air gap 550.

On the other hand, the volume of the air gap is designed so that the inter-wiring capacitance is lower than a desired level according to the distance between wirings 320. The first bottom face 520 is at a level above half of the height of the wirings 320. Consequently, the inter-wiring capacitance can be decreased regardless of the dielectric constant of the first interlayer insulating layer 310 or the second interlayer insulating layer 410.

The bottom face of the air gap 500 may be below the bottom faces of the wirings 320. In other words, the bottom face of the air gap 500 may be below the upper face of the underlying lower interlayer insulating layer 210 (or second interlayer insulating layer 410). This prevents short-circuiting between the wirings 320 due to misalignment of the via 440 and also decreases the inter-wiring capacitance of the first wirings. Among air gaps 500 located in different places, the bottom face of one air gap may be below or above that of another air gap within a given tolerance range.

Furthermore, an oxide layer (not shown) may lie between a pair of wirings 320 and the second interlayer insulating layer 410. If a metal cap layer 326 exists, an oxide layer may lie between the metal cap layer 326 and the second interlayer insulating layer 410. This oxide layer is formed over the upper face of the wiring 320 or metal cap layer 326 in the first trench formation step and the second trench formation step.

Figure 3A:
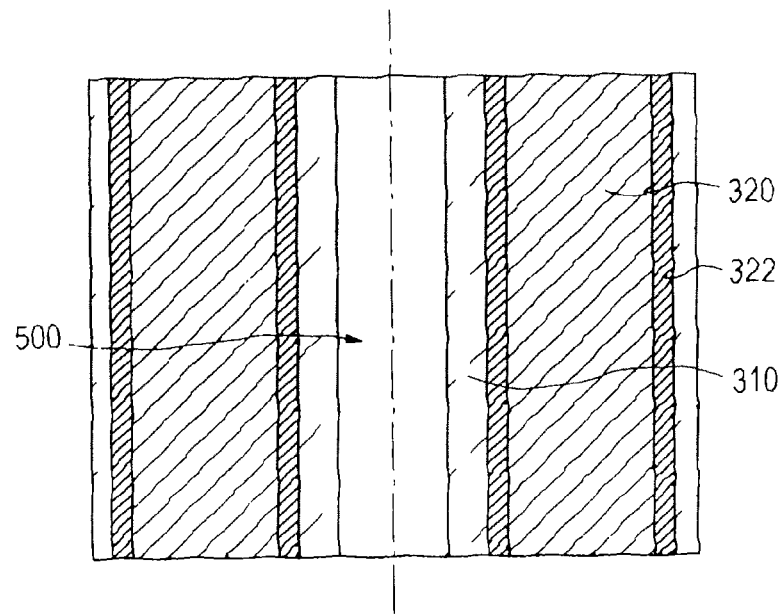
Figure 3B:
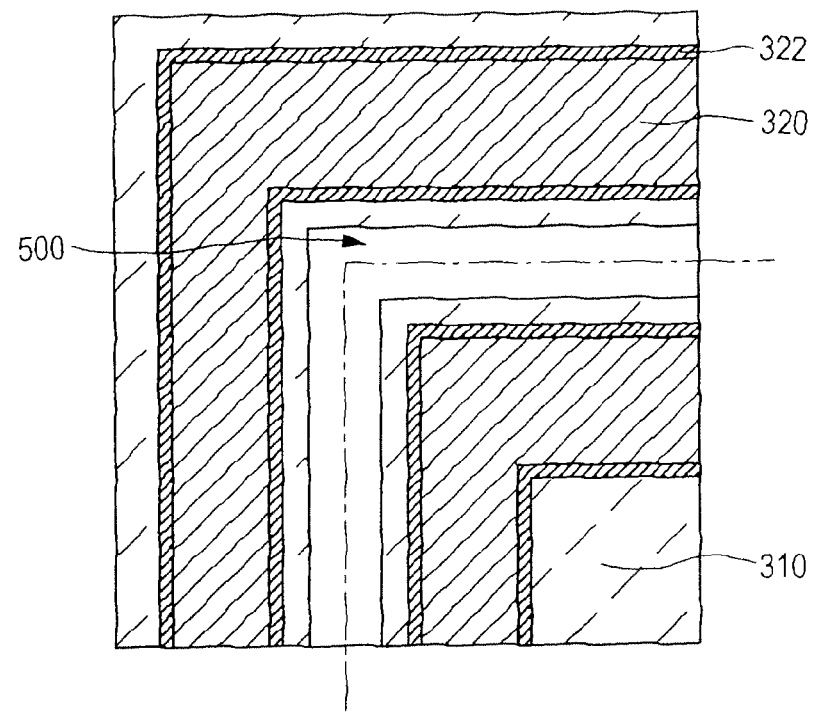

Next, the shape of the air gap 500 in a plan view will be described referring to FIGS. 3A and 3B. FIGS. 3A and 3B are enlarged plan views of the semiconductor device 10 according to the first embodiment. FIGS. 3A and 3B show the cut surfaces of the central part of the wirings 320 in a sectional view. FIG. 3A shows that the wirings 320 are linear in a plan view and FIG. 3B shows that the wirings 320 are bent in a plan view.

As shown in FIGS. 3A and 3B, the air gap 500 is located in the center of a pair of wirings 320 in a plan view. In the manufacturing method which will be described later, the pair of wirings 320 are located symmetrically with the air gap 500 between them in a self-aligning manner. This prevents short-circuiting between the wirings 320 even if either of the wirings 320 is misaligned.

As shown in FIG. 3B, when the wirings 320 are bent in a plan view, the air gap 500 is formed in a way to follow the shape of the wirings 320. If the bent portion of each wiring 320 is rounded, the bent portion of the air gap 500 is also rounded in a way to follow the shape of the wirings 320.

Figure 4:
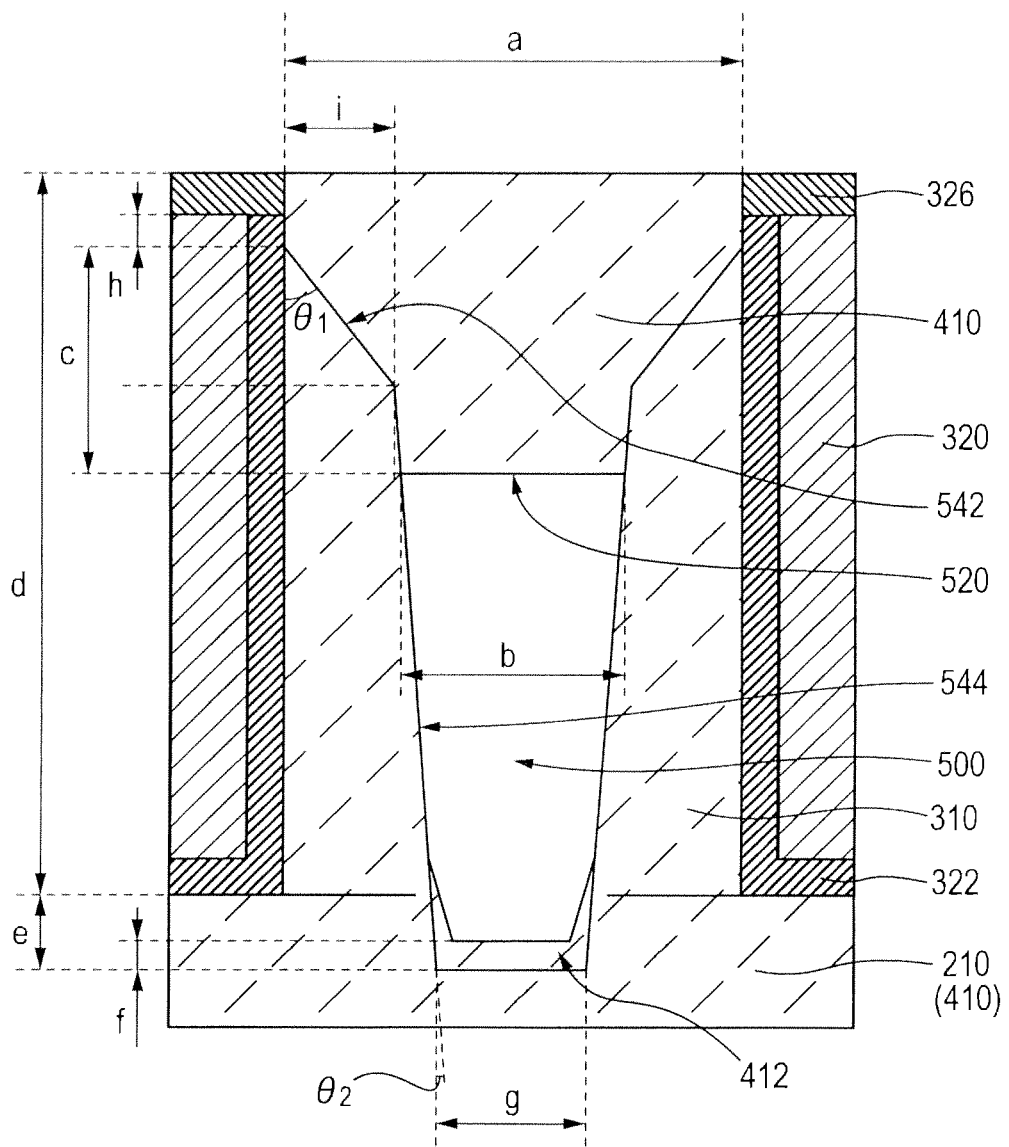
FIG. 4 is an enlarged sectional view of the semiconductor device according to the first embodiment.

Next, the dimensions of the air gap 500 will be described referring to FIGS. 4 to 6. FIG. 4 is an enlarged sectional view of the semiconductor device 10 according to the first embodiment. FIG. 4 shows "first wirings" among the wirings 320.

Figure 5:
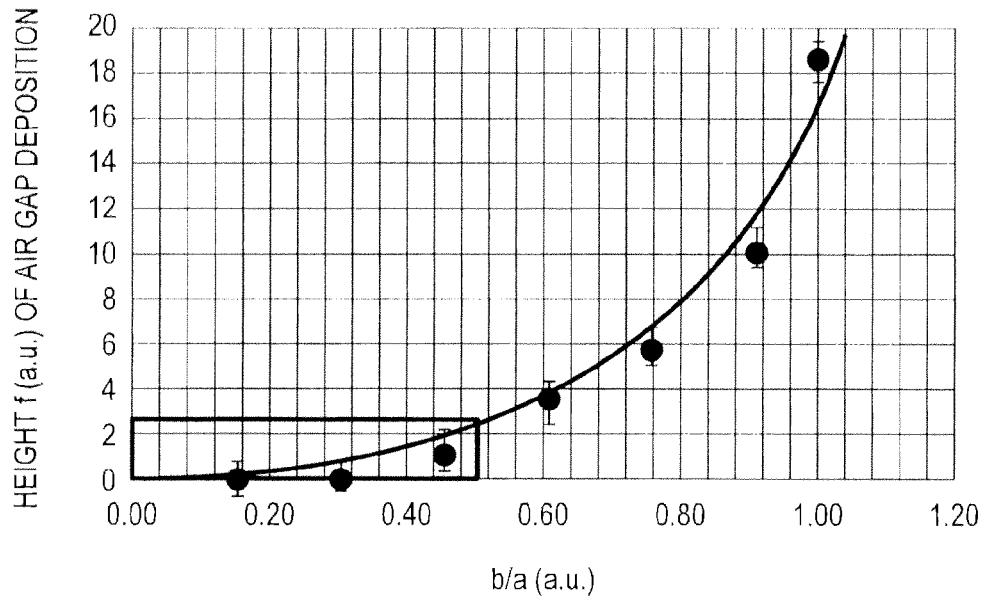
FIG. 5 is a graph which explains the shape of an air gap according to the first embodiment.
Figure 6:
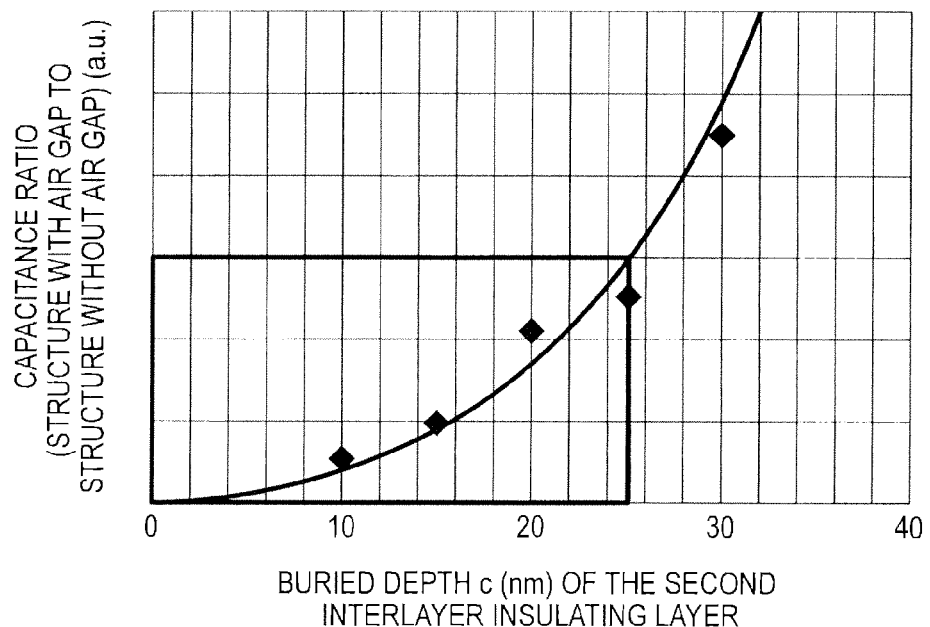
FIG. 6 is a graph which explains the shape of an air gap according to the first embodiment.

FIGS. 5 and 6 are graphs which explain the shape of the air gap 500 according to the first embodiment.

The reference signs used in FIG. 4 are explained below. In FIG. 4, a represents the distance between first wirings. In the figure, b represents the distance of the portion of the first interlayer insulating layer 310 which is in contact with the first bottom face 520. c represents the depth from the point where the upper end of the first interlayer insulating layer 310 contacts each first wiring to the lower end of the first end face 520 (buried depth of the second interlayer insulating layer 410). d represents the height of the wiring 320 including the metal cap layer 326. e represents the depth from the bottom face of the wiring 320 to the bottom face of the air gap 500. f represents the height of the second interlayer insulating layer 410 deposited on the bottom face of the air gap 500 (air gap deposition 412). g represents the width of the bottom face of the air gap 500. h represents the height from the point where the upper end of the first interlayer insulating layer 310 contacts the first wiring to the upper face of the first wiring. i represents the distance from the side face of the wiring 320 to the lower end of the first bottom face 520 in a plan view. These dimensions are in nm. The angle between the first side face 542 of the first interlayer insulating layer 310 and the side face of the first wiring is expressed as $\theta_1$. The angle between the second side face 544 of the first interlayer insulating layer 310 and a plane parallel to the side face of the first wiring is expressed as $\theta_2$.

Next, the air gap deposition 412 will be described referring to FIG. 5. In the graph of FIG. 5, the horizontal axis represents the ratio of b to a (b/a). In the graph of FIG. 5, the vertical axis represents height f of the second interlayer insulating layer 410 deposited on the bottom face of the air gap 500 (air gap deposition 412). The solid line in the graph is an approximate line.

The "air gap deposition 412" is a portion of the second interlayer insulating layer 410 which is deposited on the bottom face of the air gap 500 while the second interlayer insulating layer 410 is deposited and the first bottom face 520 is formed. When the height of the air gap deposition 412 is considered to be "large", it means that the amount of the second interlayer insulating layer 410 excessively buried in the air gap 500 is large.

As shown in FIG. 5, there is a tendency that as the ratio of b/a increases, height f of the air gap deposition 412 becomes larger. This suggests that as the area of the second trench (360, described later) in a plan view becomes larger with respect to distance a between first wirings, it becomes more difficult to make an air gap 500. The second trench (360) is a trench used to make an air gap 500. The second trench (360) will be detailed later.

The present inventors have found the conditions required to make an air gap 500 stably based on this tendency. Height f of the air gap deposition 412 sharply increases when the value of b/a is larger than 0.5. f can be approximated to an exponential function of b/a. If the value of b/a is larger than 0.5, the amount of the air gap deposition 412 in the air gap 500 would be larger. Also, the air gap deposition 412 would not be always uniform among all air gaps 500. Therefore, if the amount of the air gap deposition 412 is large, the shape of the air gap 50 might vary.

By contrast, if the value of b/a is not larger than 0.5, air gaps 500 can be formed stably. Therefore, in the first embodiment, preferably the relation of b/a≤0.5 should hold as a condition to make an air gap 500. This prevents the air gap 500 from being buried by the second interlayer insulating layer 410 and also ensures that the in-plane shape of the air gap 500 is uniform.

The absolute value of height f of the air gap deposition 412 depends on the absolute value of distance a between first wirings. For this reason, the vertical axis is in arbitrary unit (a.u.). However, the dependence of height f of the air gap deposition 412 on b/a is constant when distance a between first wirings is 40 nm or less. On the other hand, when distance a between first wirings is longer than 40 nm, the amount of the air gap deposition 412 considerably increases. Therefore, it is preferable that distance a between first wirings be 40 nm or less. If so, an air gap 500 can be formed stably as mentioned above.

The distance b of the portion of the first interlayer insulating layer 310 which is in contact with the first bottom face 520 can be controlled by controlling the width of the bottom face of the first trench 350 which will be described later.

Next, buried depth c of the second interlayer insulating layer 410 will be described referring to FIG. 6. In FIG. 6, the horizontal axis represents buried depth c of the second interlayer insulating layer 410. In FIG. 6, the vertical axis represents the inter-wiring capacitance ratio of a structure with an air gap 500 (first embodiment) to a structure without an air gap 500 (hereinafter referred to as "capacitance ratio"). Here the "structure without an air gap 500" is the same as the first embodiment except that it has no air gap 500. The solid line in the graph is an approximate line.

The "inter-wiring capacitance of the structure with an air gap 500" depends on the volume of the air gap 500. Therefore, the capacitance ratio depends on buried depth c of the second interlayer insulating layer 410.

As shown in FIG. 6, there is a tendency that as the value of buried depth c of the second interlayer insulating layer 410 increases, the capacitance ratio becomes larger. In other words, as the position of the first bottom face 520 of the second interlayer insulating layer 410 is deeper, the volume of the air gap 500 is smaller. Thus the capacitance ratio tends to be larger as the value of depth c is larger.

The absolute value of capacitance ratio depends, for example, on the absolute value of height d of wiring 320. The vertical axis is in arbitrary unit (a. u.). However, the dependence of the capacitance ratio on buried depth c of the second interlayer insulating layer 410 remains unchanged regardless of height d of wiring 320.

Furthermore, based on this tendency, the inventors have found the conditions required to decrease the inter-wiring capacitance in the first embodiment stably. If the value of buried depth c is larger than 25 nm, the capacitance ratio sharply increases regardless of height d of wiring 320. In this case, the air gap 500 would be less effective in decreasing inter-wiring capacitance. Also, if the value of buried depth c of the second interlayer insulating layer 410 is larger than the above value, the first bottom face 520 would be not always uniform among all air gaps 500 in terms of position and shape. In this case, inter-wiring capacitance might vary from one wiring 320 to another.

By contrast, when buried depth c of the second interlayer insulating layer 410 is 25 nm or less, the air gap 500 is effective in decreasing inter-wiring capacitance stably regardless of height d of wiring 320.

On the other hand, if the via 440 is misaligned, the position of the lower end of the misaligned via 440 varies depending on the etching conditions for the via 440. Specifically, for example, the position of the lower end of the misaligned via 440 is less than 10 nm below the upper face of the wiring 320. If the value of buried depth c of the second interlayer insulating layer 410 is smaller than 10 nm, the via 440 might contact the air gap 500. Therefore, it is preferable that the value of buried depth c of the second interlayer insulating layer 410 be 10 nm or more. This prevents contact of the via 440 with the air gap 500.

For the above reason, buried depth c (nm) of the second interlayer insulating layer 410 should meet the following requirement: $10 \leq c \leq 25$.

Other parameters will be explained, referring back to FIG. 4. Distance i from the side face of the wiring 320 to the lower end of the first bottom face 520 in a plan view can be controlled by the etching conditions in the first trench formation step and second trench formation step. Specifically, distance i is, for example, not less than 10 nm and not more than 20 nm. When distance i is not less than 10 nm, the via 440 is prevented from overlapping the air gap 500 in a plan view. Specifically, if the via 440 is misaligned, the via 440 is less likely to contact the air gap 500. On the other hand, when distance i is not more than 20 nm, the inter-wiring capacitance can be decreased without reducing the air gap 500 excessively. Due to production tolerance, the left and right distances i with the air gap 500 between them are not always equal to each other.

Angle $\theta_1$ between the first side face 542 and the side face of a first wiring and angle $\theta_2$ between the second side face 544 of the first interlayer insulating layer 310 and a plane parallel to the side face of the first wiring can also be controlled by the etching conditions in the first trench formation step and second trench formation step. Angles $\theta_1$ and $\theta_1$ exert an influence on b/a, depth c, etc. as mentioned above. Here, "angle $\theta_1$ between the first side face 542 and the side face of a first wiring" refers to the angle of the first side face 542 in the tangential direction where it contacts the side face of the first wiring. Also, "angle $\theta_2$ between the second side face 544 of the first interlayer insulating layer 310 and a plane parallel to the side face of the first wiring" refers to the angle between the tangential direction where the second side face 544 contacts the bottom face of the air gap 500 and a plane parallel to the side face of the first wiring.

Angle $\theta_1$ between the first side face 542 and the side face of the first wiring is larger than angle $\theta_2$ between the second side face 544 and a plane parallel to the side face of the first wiring. This makes it possible to fill the upper face of the air gap 500 with the second interlayer insulating layer 410.

Specifically, for example, angle $\theta_1$ between the first side face 542 and the side face of the first wiring is not less than 20 degrees and not more than 45 degrees. When angle $\theta_1$ is not less than 20 degrees, the relation of $b/a \leq 0.5$ can be satisfied. Also, when $\theta_1$ is not more than 45 degrees, only the bottom face 352 can be selectively etched without etching the first side face 542 excessively in the second trench formation step which will be described later.

Also, for example, angle $\theta_2$ between the second side face 544 of the first interlayer insulating layer 310 and a plane parallel to the side face of the first wiring is not more than 20 degrees. If angle $\theta_2$ is more than 20 degrees, the amount of air gap deposition 412 embedded in the air gap 500 tends to be larger. This means that when angle $\theta_2$ is not more than 20 degrees, the upper face of the air gap 500 can be stably filled with the second interlayer insulating layer 410. Alternatively, the area where the first side face 542 contacts the second side face 544 may be reversely tapered as in the third embodiment.

Height h from the point where the upper end of the first interlayer insulating layer 310 contacts the first wiring to the upper face of the first wiring can be controlled by the etching conditions in the first trench formation step and second trench formation step. Concretely, height h is not less than 3 nm and not more than 10 nm.

Next, a method of manufacturing a semiconductor device according to the first embodiment will be described referring to FIGS. 7 to 11B. The method of manufacturing a semiconductor device according to the first embodiment includes the following steps. First, a first interlayer insulating layer 310 is formed over a semiconductor substrate 100. Then, a plurality of wiring gutters are made in the first interlayer insulating layer 310 and metal is buried in the wiring gutters to form a plurality of wirings 320 (wiring formation step). Then, by etching back the first interlayer insulating layer 310 using the wirings 320 as a mask, a first trench 350 is formed between at least one pair of wirings 320 in the first interlayer insulating layer 310 (first trench formation step), in which the trench has first side faces 542 in contact with wirings 320 and a bottom face 352 between the first side faces. Then, a second trench 360 is formed in the first interlayer insulating layer 310 by anisotropically etching at least the bottom face 352 of the first trench 350 selectively (second trench formation step). Then, a second interlayer insulating layer 410 is formed over the wirings 320 and first interlayer insulating layer 310 and an upper portion of the second trench 360 is filled to make an air gap 500 between at least one pair of wirings 320 in the first interlayer insulating layer 310. Details are given below.

Figure 7:
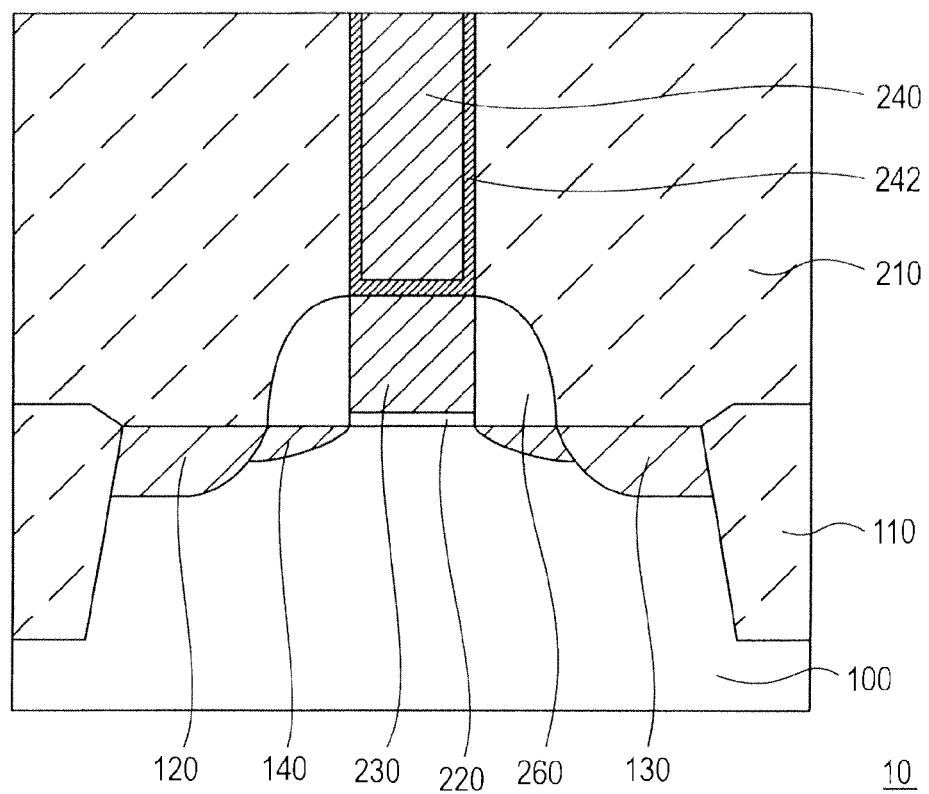
FIG. 7 is a sectional view illustrating a method of manufacturing a semiconductor device according to the first embodiment.

First, as shown in FIG. 7, an element isolation region 110 with an opening (not designated by a reference sign in the figure) is formed in the semiconductor substrate 100. Then, a MISFET including a gate insulating layer 220, gate electrode 230, extension regions 140, source region 120, and drain region 130 is formed in the opening.

Then, a lower interlayer insulating layer 210 is formed over the semiconductor substrate 100, element isolation region 110, sidewall insulating film 260, and gate electrode 230, for example, by a CVD (Chemical Vapor Deposition) process. Then, the upper face of the lower interlayer insulating layer 210 of the lower interlayer insulating layer 210 is planarized by a CMP (Chemical Mechanical Polishing) process. For example, the lower interlayer insulating layer 210 is made of the same material as the material of the first interlayer insulating layer 310 which will be described later.

Next, a contact hole (not shown) is made in the lower interlayer insulating layer 210 in a way to overlap the gate electrode 230 in a plan view by etching the lower interlayer insulating layer 210, for example, by an RIE (Reactive Ion Etching) process. Also a contact hole (not shown) is made in a region (not shown) of the lower interlayer insulating layer 210 in a way to overlap the source region 120 and drain region 130 in a plan view.

Next, a barrier metal layer 242 is formed on each of the contact holes. Then, metal film (not designated by a reference sign in the figure) is formed by a CVD process to fill the contact hole. Then, the metal film is polished by a CMP process to bury metal in the contact hole. The upper face of the lower interlayer insulating layer 210 may be planarized. A contact plug 240 is thus completed in the lower interlayer insulating layer 210.

Figure 8A:
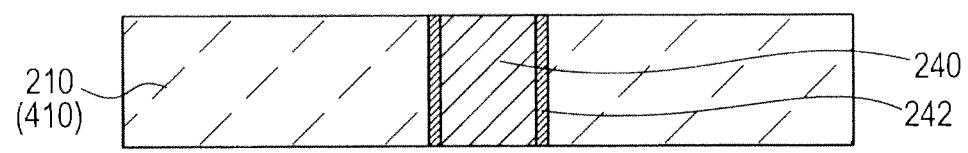

FIG. 8A shows part of what is shown in FIG. 7, in which the semiconductor device formed in the semiconductor substrate 100 is omitted.

Figure 8B:
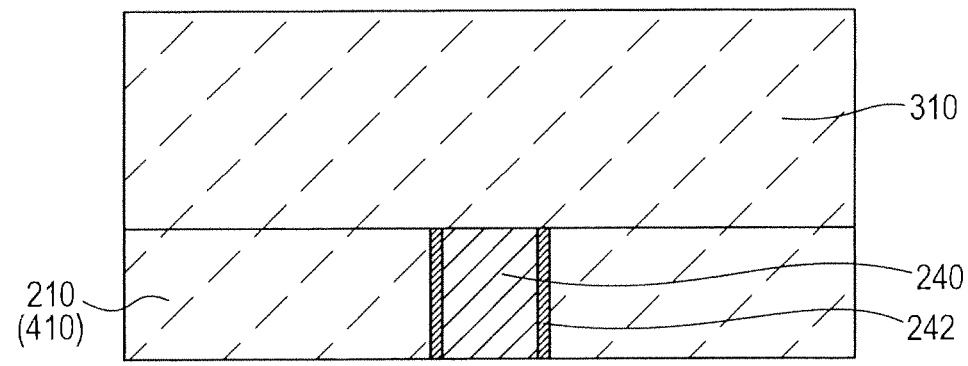

As shown in FIG. 8B, a first interlayer insulating layer 310 is formed over the lower interlayer insulating layer 210, for example, by a CVD process. Alternatively the first interlayer insulating layer 310 may be formed by coating.

Figure 9A:
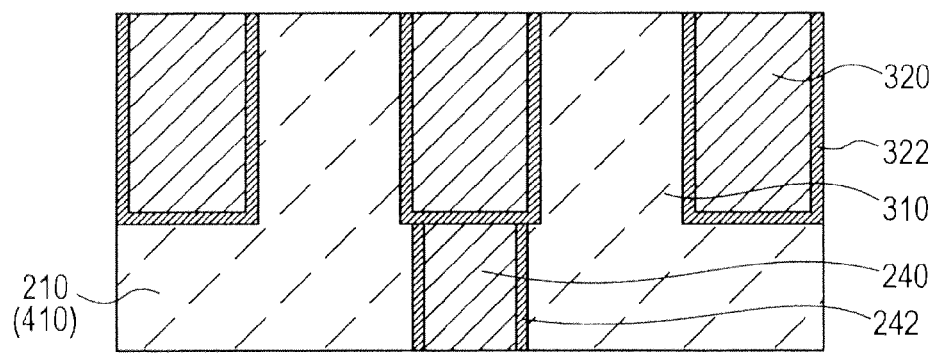

Next, as shown in FIG. 9A, a plurality of wiring gutters (not designated by a reference sign in the figure) are made by etching the first interlayer insulating layer 310, for example, by an RIE process. Then, a barrier metal layer 322 is formed on each of the wiring gutters. For example, a wiring gutter is made in a way to overlap the contact plug 240 in a plan view. Then, metal film (not designated by a reference sign in the figure) to fill the wiring gutter is formed, for example, by plating. Then, the metal film is polished by a CMP process to bury metal in the wiring gutter. The upper face of the first interlayer insulating layer 310 may be planarized by a CMP process. A plurality of wirings 320 are thus formed in the first interlayer insulating layer 310 (wiring formation step).

Figure 9B:
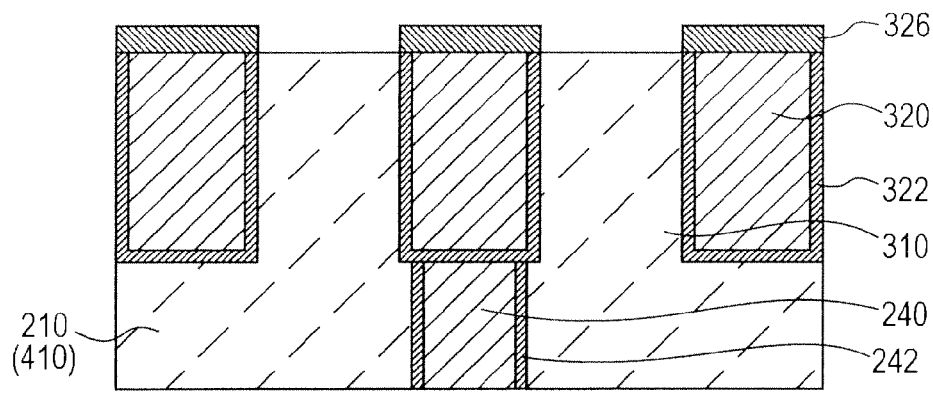

Next, as shown in FIG. 9B, a cap layer is formed over each wiring 320 after the wiring gutter formation step and before the first trench formation step (described later). Here, for example, a metal cap layer 326 as a cap layer is selectively grown over the wiring 320 (metal cap layer formation step). The cap layer functions as a mask for etching the first interlayer insulating layer 310. The cap layer also functions as a copper (Cu) diffusion prevention film. In this case, by selectively growing the metal cap layer 326 as a cap layer, the metal cap layer 326 can be formed in a self-aligning manner in a way to overlap the wiring 320 in a plan view without a photolithographic process.

Figure 10A:
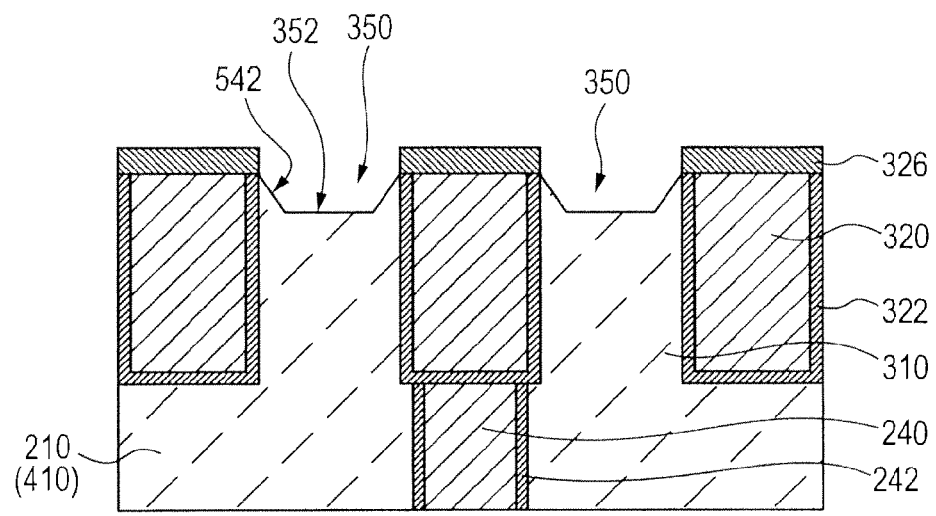

Next, as shown in FIG. 10A, the first interlayer insulating layer 310 is etched back using the wirings and metal cap layers 326 as a mask. Consequently, a first trench 350 is formed between at least one pair of wirings 320 in the first interlayer insulating layer 310, in which the trench has first side faces 542 in contact with wirings 320 and a bottom face 352 between the first side faces 542 (first trench formation step). At this time, the bottom face 352 of the first trench 350 is formed in the center between the pair of wirings 320 in a plan view. The first trench 350 has, for example, a trapezoidal shape with its long side up in a sectional view. At the same time a forward tapered first side face 542 is formed.

In the first trench formation step, for example, CHF gas or CF gas is used as etching gas. Preferably the applied voltage should be not less than 100 W and not more than 200 W. By etching under these conditions, the first trench 350 which meets the above dimensional requirement of the air gap 500 can be formed.

Figure 10B:
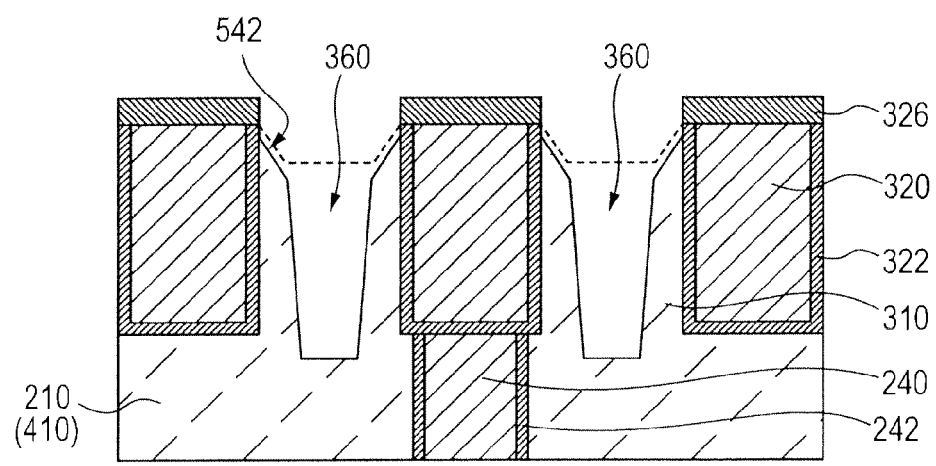

Next, as shown in FIG. 10B, a second trench 360 is formed in the first interlayer insulating layer 310 by anisotropically etching at least the bottom face 352 of the first trench 350 selectively (second trench formation step). In other words, etching is done on the first interlayer insulating layer 310 using the wirings 320 and first side faces 542 as a mask. The dotted lines in the figure represent the location of the first trench 350.

In the second trench formation step, for example, etching is done at lower pressure than in the first trench formation step. This makes the etching selectivity in the direction perpendicular to the surface of the semiconductor substrate 100 higher than in the first trench formation step. Concretely, etching is done at 10 mTorr or more and 30 mTorr or less in the second trench formation step.

In the second trench formation step, for example, etching is done at higher input power than in the first trench formation step. This makes the etching selectivity in the direction perpendicular to the surface of the semiconductor substrate 100 higher than in the first trench formation step. Concretely, etching is done at 200 W or more and 500 W or less in the second trench formation step.

In the second trench formation step, for example, CHF gas, CF gas, or SF gas is used as etching gas.

In the second trench formation step, the position of the bottom face of the second trench 360 is controlled, for example, by etching time. The second trench 360 is formed so that the bottom face of the air gap 500 is below the bottom face of the wiring 320.

In the second trench formation step, the first side face 542 is also etched. For this reason, the first interlayer insulating layer 310 is formed so that its upper end is below the upper face of the first wiring. As a result of the first trench formation step and second trench formation step, the first interlayer insulating layer 310 lying between first wirings (wirings 320) is shaped so as to have angle $\theta_1$ between the first side face 542 and the side face of the first wiring and angle $\theta_2$ between the second side face 544 of the first interlayer insulating layer 310 and a plane parallel to the side face of the first wiring. In other words, the first interlayer insulating layer 310 lying between first wirings (wirings 320) is shaped like sidewalls of the first wirings (wirings 320) in a self-aligning manner.

Figure 11A:
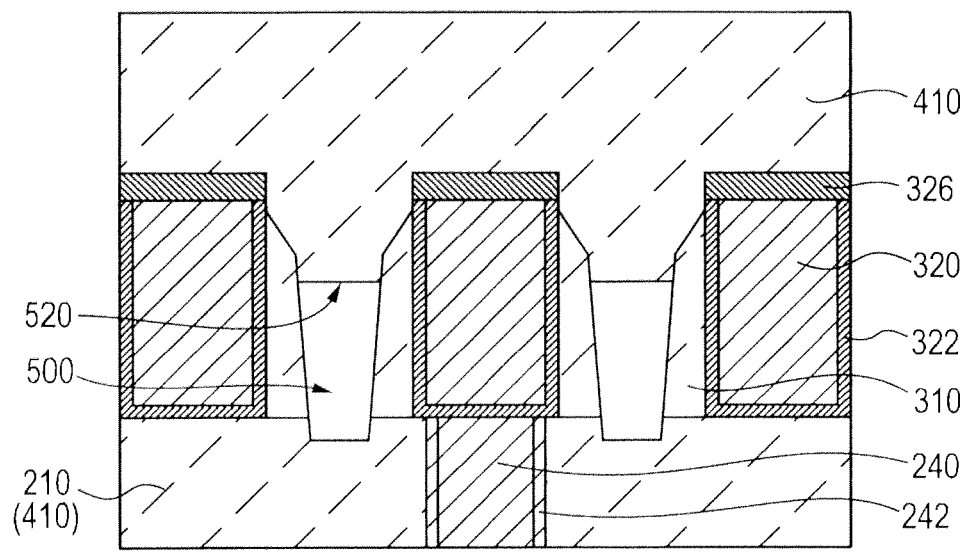

Next, as shown in FIG. 11A, a second interlayer insulating layer 410 is formed over the wirings 320 and first interlayer insulating layer 310, for example, by a CVD process (second interlayer insulating formation step). Here, for example, the second interlayer insulating layer 410 is made of the same material as the first interlayer insulating layer 310. At the same time, an air gap 500 is made between at least one pair of wirings 320 in the first interlayer insulating layer 310 by filling the upper portion of the second trench 360. Here, "filling the upper portion of the second trench 360" refers to closing the upper portion of the second trench 360.

As described above, an air gap 500 can be made without a lithographic process during the first trench formation step, the second trench formation step and the step of forming the second interlayer insulating layer. The process from the first trench formation step to the second trench formation step may be carried out consistently in a vacuum condition. Furthermore, the first trench formation step and second trench formation step may be carried out by an etching apparatus. This contributes to shortening the manufacturing time. Since the vacuum is not broken, the reliability of the semiconductor device 10 can be improved.

Figure 11B:
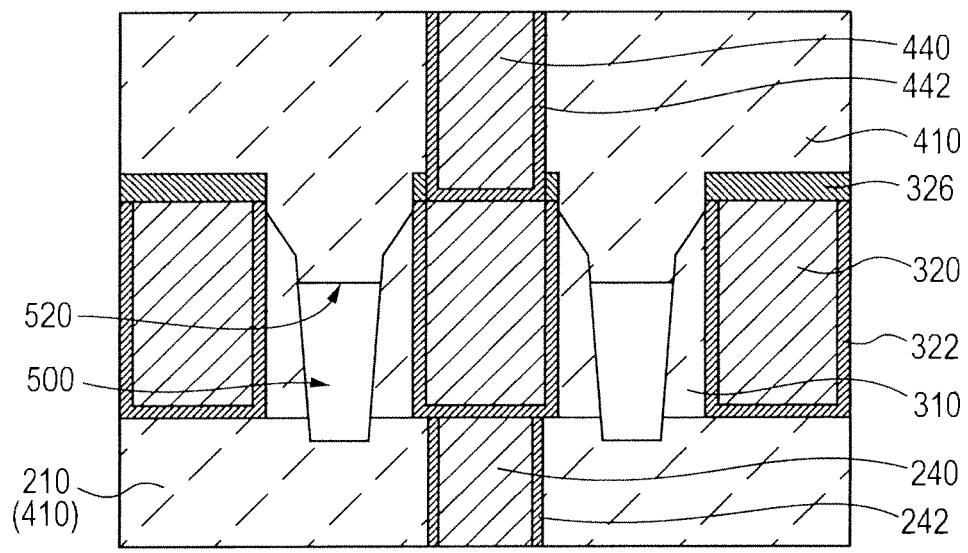

Next, as shown in FIG. 11B, a via hole (not shown) is made in a way to overlap the wiring 320 in a plan view by etching the first interlayer insulating layer 310, for example, by an RIE process. Then, a barrier metal layer 442 is formed on the via hole. Then, metal film (not designated by a reference sign in the figure) to fill the via hole is formed, for example, by plating. Then, the metal film is polished by a CMP process to fill metal in the via hole. The metal is, for example, Cu. The upper face of the second interlayer insulating layer 410 may be planarized by a CMP process. A via 440 is thus formed in the second interlayer insulating layer 410.

Next, another first interlayer insulating layer 310 is formed over the second interlayer insulating layer 410. A multilayer wiring structure having an air gap 500 may be further formed over it. Also, bump electrodes (not shown) may be formed over the uppermost layer of the multilayer wiring structure.

Figure 12A:
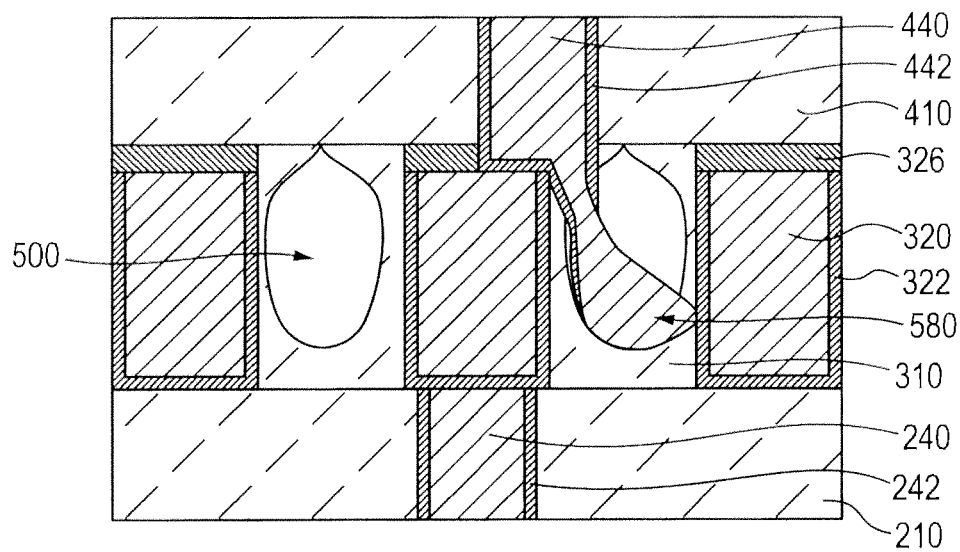
Figure 12B:
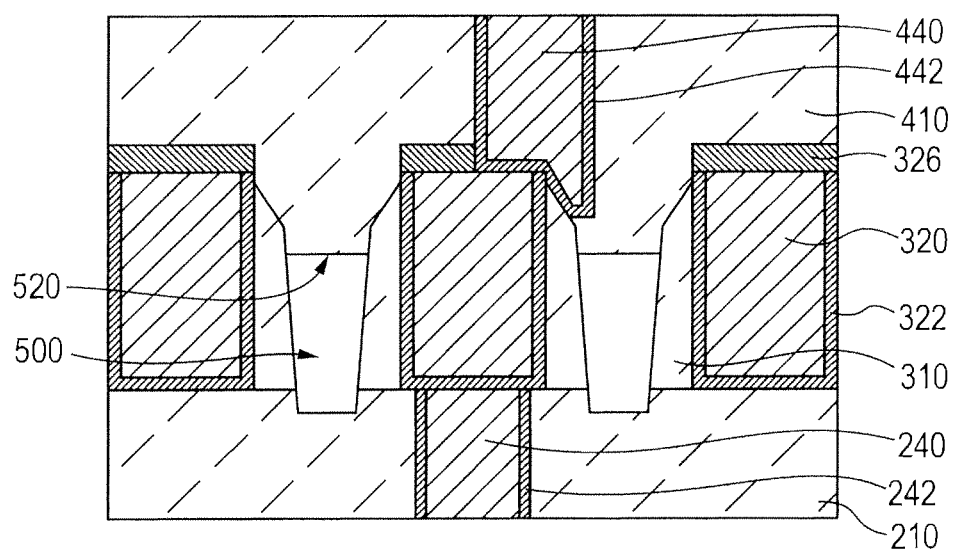

Next, the advantageous effect of the first embodiment will be described referring to FIGS. 12A and 12B. FIG. 12A is a sectional view of a semiconductor device 10 as a comparative example. FIG. 12B is a sectional view of a semiconductor device 10 according to the first embodiment. Both the figures show that the via 440 is misaligned.

The semiconductor device 10 as a comparative example which is shown in FIG. 12A is the same as the one according to the first embodiment except that an air gap 500 is made as described below. In the step of forming the first interlayer insulating layer 310 in the comparative example, the air gap 500 is made in the first interlayer insulating layer 310 by adjusting CVD conditions.

As shown in FIG. 12A, the air gap 500 in the comparative example is oval in a sectional view. The upper face of the air gap 500 is above the upper faces of the wirings 320.

In the comparative example, if the diameter of the via 440 becomes larger due to misalignment of the via 440 or production tolerance, the lower end of the via hole will contact the upper face of the air gap 500 in the step of making the via 440. If so, etching gas enters the air gap 500, causing the air gap 500 to expand to an adjacent or underlying wiring 320. The next step is to fill metal in the via hole to make a via 440. At this time, if the via 440 is misaligned, it may be short-circuited with an adjacent or underlying wiring 320. FIG. 12A shows a case that the misaligned via 440 is in contact with the adjacent wiring 320, forming a short-circuit 580.

An air gap 500 can be made in the first interlayer insulating layer 310 by a method different from the method in the comparative example. One alternative method is the method as described in Japanese Unexamined Patent Publication No. 2007-141985 in which a sacrificial film pillar as a selectively removable insulating film is formed in the region for the formation of a via. However, in this method, it is difficult to obtain the required volume of the air gap 500. Therefore, there is a possibility that the inter-wiring capacitance can not be decreased to a desired level. Besides, in the method as described in Japanese Unexamined Patent Publication No. 2007-141985, the number of photolithographic steps is larger than in the process of making a structure without an air gap 500 and longer manufacturing time is thus required.

On the other hand, in the first embodiment, as shown in FIG. 12B, the upper ends of the first interlayer insulating layer 310 between adjacent first wirings whose distance is shortest are in contact with the side faces of the first wirings. The first bottom face 520 is below the upper faces of the first wirings. Here, the relation of b/a≤0.5 is satisfied, where a represents the distance between the first wirings and b represents the distance of the portion of the first interlayer insulating layer 310 which is in contact with the first bottom face 520. Consequently, the misaligned via 440 is formed in the second interlayer insulating layer 410 in contact with the first wiring. In other words, the misaligned via 440 does not contact the air gap 500. Therefore, the misaligned via 440 and the wiring 320 are not short-circuited through the air gap 500.

The air gap 500 is made using the wirings 320 as a mask in a self-aligning manner. As mentioned above, a special photolithographic step is not required, so manufacturing time can be shortened. This ensures high mass productivity.

As discussed above, according to the first embodiment, it is possible to provide a semiconductor device 10 in which misalignment does not cause short-circuiting and inter-wiring capacitance is decreased.

Second Embodiment

Figure 13:
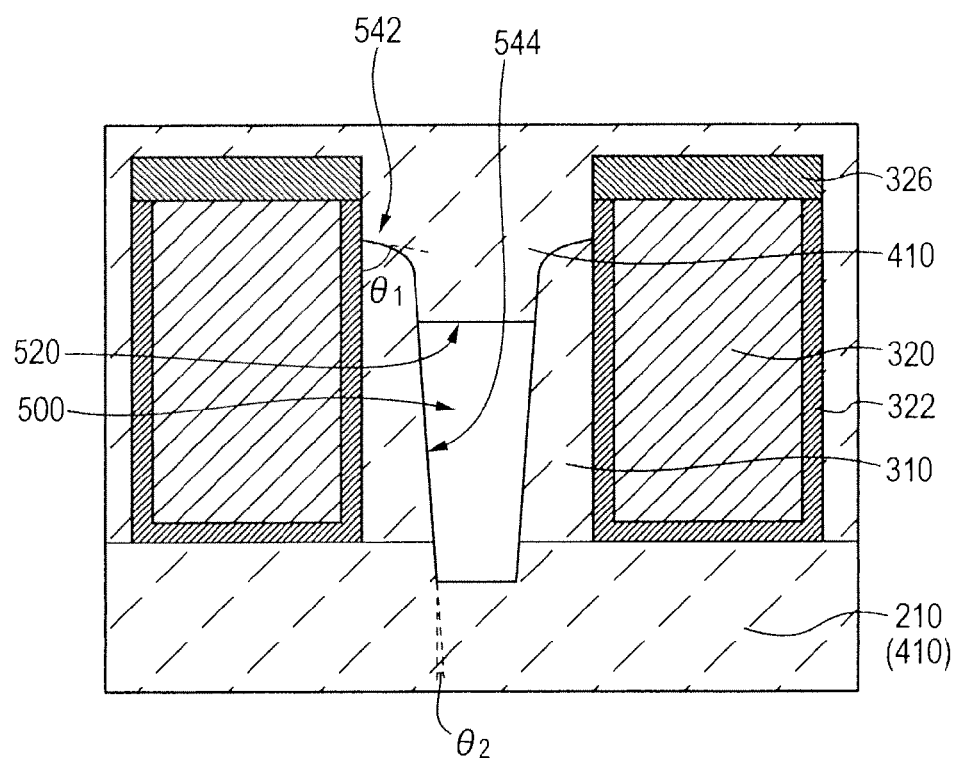
FIG. 13 is an enlarged sectional view of a semiconductor device according to a second embodiment of the invention.

FIG. 13 is an enlarged sectional view of a semiconductor device 10 according to the second embodiment. The second embodiment is the same as the first embodiment except that the first side face 542 is a curved surface. Details are given below.

As shown in FIG. 13, the first side face 542 may be a curved surface. Specifically, the first side face 542 is curved from the portion of the first interlayer insulating layer 310 in contact with a wiring 320 toward its portion exposed to the air gap 500.

Here, as mentioned above, "angle $\theta_1$ between the first side face 542 and the side face of the first wiring" is the angle in the tangential direction of the portion of the first side face 542 in contact with the side face of the first wiring.

The second side face 544 may also be a curved surface. Specifically, the second side face 544 may be curved from the portion of the first interlayer insulating layer 310 in contact with the first bottom face 520 toward the bottom face of the air gap 50.

The method of manufacturing the semiconductor device 10 according to the second embodiment is the same as in the first embodiment except the second trench formation step. The initial steps and first trench formation step are carried out in the same way as in the first embodiment to make a flat first trench 350 in the first interlayer insulating layer 310 as in the first embodiment.

In the second trench formation step, the etching selectivity in a direction perpendicular to the surface of the semiconductor substrate 100 is increased. In this step, the first side face 542 of the first trench 350 is etched. The first side face 542 is curved from the portion of the first interlayer insulating layer 310 in contact with a wiring 320 toward its portion exposed to the air gap 500.

The subsequent steps are the same as in the first embodiment.

The second embodiment brings about the same advantageous effect as the first embodiment. The air gap 500 may be formed into different shapes under different etching conditions as in the second embodiment.

Third Embodiment

Figure 14:
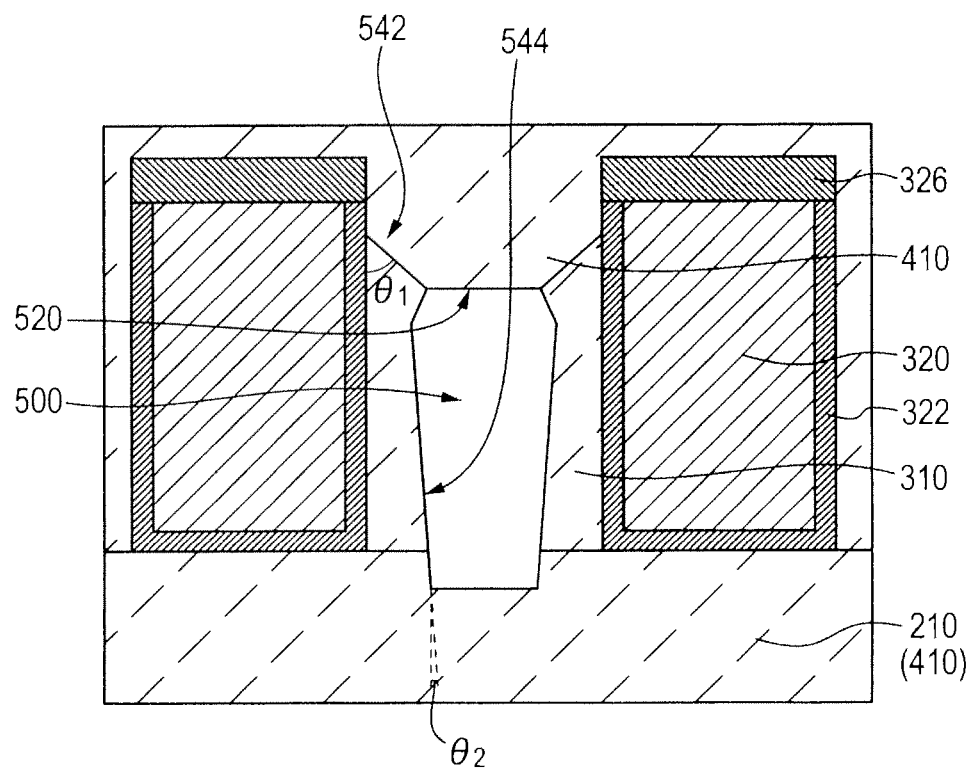
FIG. 14 is an enlarged sectional view of a semiconductor device according to a third embodiment of the invention.

FIG. 14 is an enlarged sectional view of a semiconductor device 10 according to the third embodiment. The third embodiment is the same as the first embodiment except that the diameter of a central portion of the air gap 500 expands toward a pair of wirings 320 in a sectional view. Its details are given below.

As shown in FIG. 14, for example, the portion of the second side face 544 which is in contact with the first bottom face 520 is reversely tapered. Consequently the diameter of the central portion of the air gap 500 expands toward the pair of wirings 320 in a sectional view. In other words, the air gap 500 partially overlaps the first interlayer insulating layer 310 in a plan view.

The first bottom face 520 is in contact with the inflection point between the first side face 542 and the reversely tapered portion of the second side face 544. Alternatively, the first bottom face 520 may be above or below the inflection pint.

The method of manufacturing the semiconductor device 10 according to the third embodiment is the same as in the first embodiment except that the etching conditions in the second trench formation step are different. The initial steps and first trench formation step are carried out in the same way as in the first embodiment to make a flat first trench 350 in the first interlayer insulating layer 310 as in the first embodiment.

In the early stage of the second trench formation step, a second trench 360 is formed by anisotropically etching the bottom face 352 of the first trench 350 selectively. Then, the second side face 544 of the second trench 360 is isotropically etched to expand its diameter toward the pair of wirings 320.

The subsequent steps are the same as in the first embodiment.

The third embodiment brings about the same advantageous effect as the first embodiment. The diameter of the central portion of the air gap 500 may expand toward the pair of wirings 320 as in the third embodiment. Consequently the inter-wiring capacitance can be smaller than in the first embodiment.

Alternatively, in the third embodiment, an air gap 500 may be made in advance during the step of forming the first interlayer insulating layer 310. If that is the case, the second trench 360 should be made to contact the previously made air gap 500 in the first trench formation step or second trench formation step.

Fourth Embodiment

Figure 15:
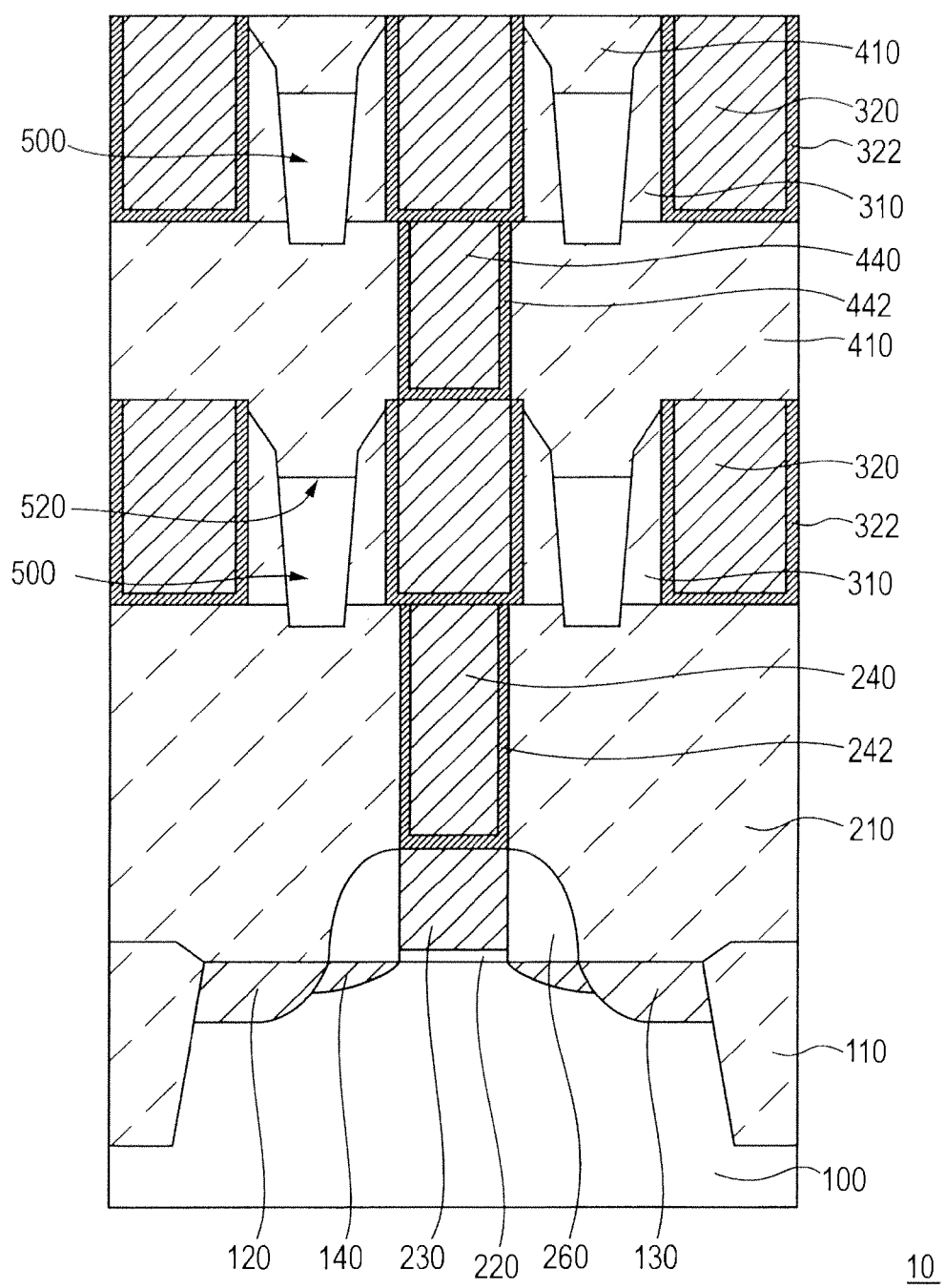
FIG. 15 is a sectional view showing the structure of a semiconductor device according to a fourth embodiment of the invention.

FIG. 15 is a sectional view showing the structure of a semiconductor device 10 according to the fourth embodiment. The fourth embodiment is the same as the first embodiment except the absence of a metal cap layer 326. Details are given below.

As shown in FIG. 15, no metal cap layer 326 is provided. The upper face of each wiring 320 is in contact with the second interlayer insulating layer 410.

The wirings 320 in the fourth embodiment contain, for example, AL or W. If each wiring 320 is made of Cu and the width of the wiring 320 is smaller than the mean free path of electrons in Cu, the resistivity of the wiring 320 is higher than when the wiring 320 contains Al or W. Hence, the embodiment is particularly useful when the width of the wiring 320 is smaller than the mean free path of electrons in Cu. If the wiring 320 contains Al or W, the wiring 320 is not etched in the first trench formation step.

Furthermore, an oxide layer (not shown) may be formed between a pair of wirings 320 and the second interlayer insulating layer 410. This oxide layer is formed over the upper faces of the wirings 320 in the first trench formation step and second trench formation step.

The method of manufacturing the semiconductor device 10 according to the fourth embodiment is the same as in the first embodiment except that a metal cap layer 326 is not formed. The second interlayer insulating layer 410 may include a plurality of layers. If that is the case, the second interlayer insulating layer 410 may be, for example, multilayer insulating film with a low-k film over an anti-diffusion film. The anti-diffusion film is, for example, nitrogen-containing silicon film such as SiN film, SiCN film, SiOCN film, SiON film or SiC film. The low-k film is, for example, silicon film containing carbon and oxygen or porous insulating film.

The fourth embodiment brings about the same advantageous effect as the first embodiment. Since the fourth embodiment does not include the step of forming a metal cap layer 326, the manufacturing time can be shorter than in the first embodiment.

Fifth Embodiment

Figure 16:
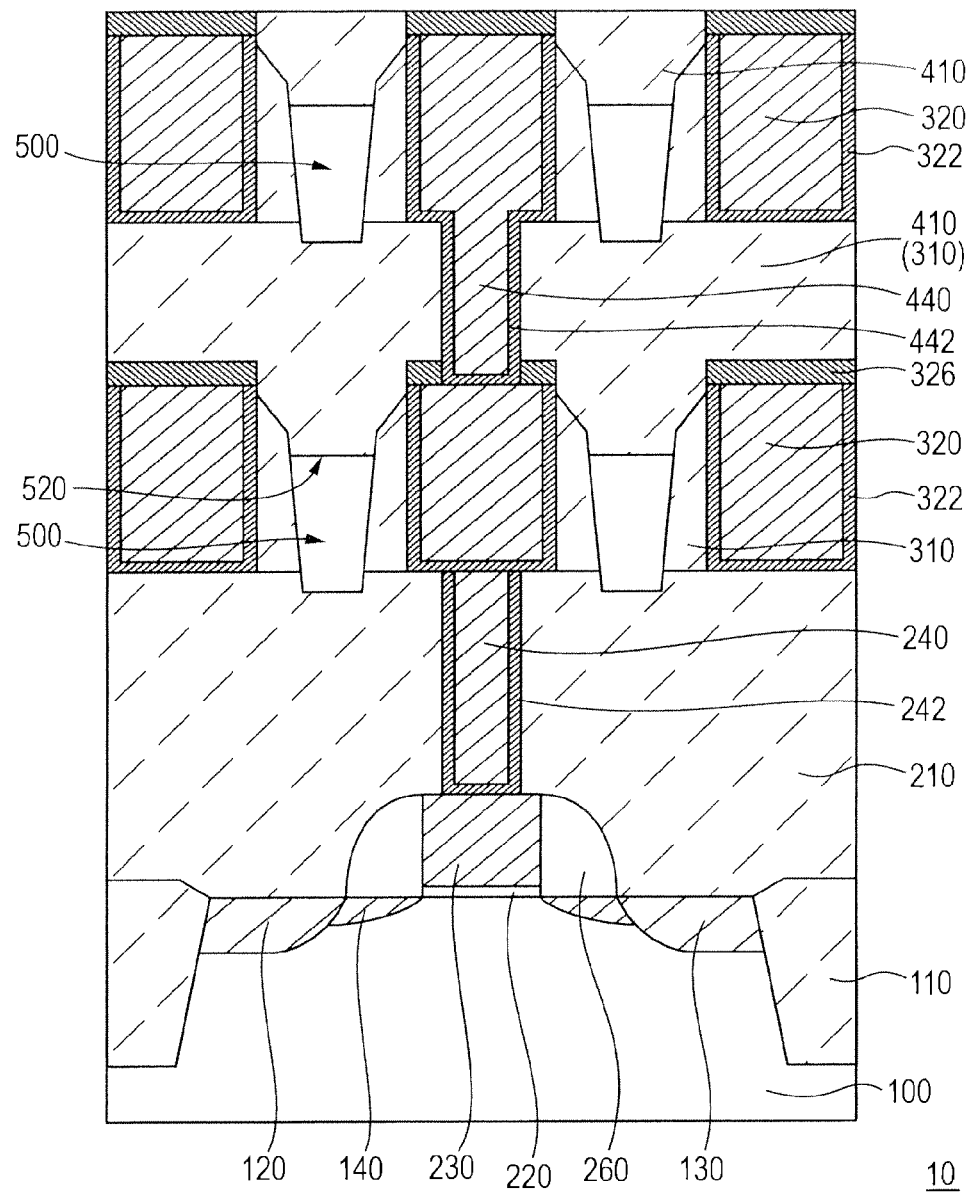
FIG. 16 is a sectional view showing the structure of a semiconductor device according to a fifth embodiment of the invention.

FIG. 16 is a sectional view showing the structure of a semiconductor device 10 according to the fifth embodiment. The fifth embodiment is the same as the first embodiment except that wirings 320 and vias 440 are formed in at least one wiring layer by a dual damascene process. Details are given below.

Like the first embodiment, a first interlayer insulating layer 310 is formed over the lower interlayer insulating layer 210 as shown in FIG. 16. An air gap 500 is made between at least one pair of wirings 320 in the first interlayer insulating layer 310. A second interlayer insulating layer 410 is formed over the wirings 320 and the first interlayer insulating layer 310.

The thickness of the second interlayer insulating layer 410 is larger than the height of the wirings 320. The second interlayer insulating layer 410 also functions as an upper first interlayer insulating layer (310).

A plurality of wirings 320 are provided in the second interlayer insulating layer 410 (which is equivalent to the first interlayer insulating layer 310 for the wirings 320 in the upper layer). At least one wiring 320 is in contact with a via 440 provided in the second interlayer insulating layer 410 (310). The via 440 is in contact with a wiring 320 in the lower layer.

These wirings 320 and via 440 are formed, for example, by a dual damascene process. The wirings 320 contain, for example, Cu. A barrier metal layer 442 may lie on the side faces and bottom faces of the wirings 320 and the side faces and bottom face of the via 440.

An air gap 500 is made between at least one pair of wirings 320 in the second interlayer insulating layer 410 (310). The structure of the air gap 500 and its vicinity is the same as in the first embodiment.

The method of manufacturing the semiconductor device 10 according to the fifth embodiment includes the following steps.

Like the first embodiment, a first interlayer insulating layer 310, wirings 320, and air gaps 500 are formed over a lower interlayer insulating layer 410. Then, a second interlayer insulating layer 410 (310) is formed over the wirings 320 and first interlayer insulating layer 310, for example, by a CVD process.

Next, wiring gutters and via holes (not designated by reference signs in the figure) are formed in the second interlayer insulating layer 410 (310). The method of making wiring gutters and via holes may be a so-called via-first process, trench-first process or middle-first process.

The method of making an air gap 500 between a pair of wirings 320 formed by the dual damascene process is the same as in the first embodiment.

The fifth embodiment brings about the same advantageous effect as the first embodiment. According to the fifth embodiment, various techniques can be used to form wirings 320 and vias 440.

Sixth Embodiment

Figure 17:
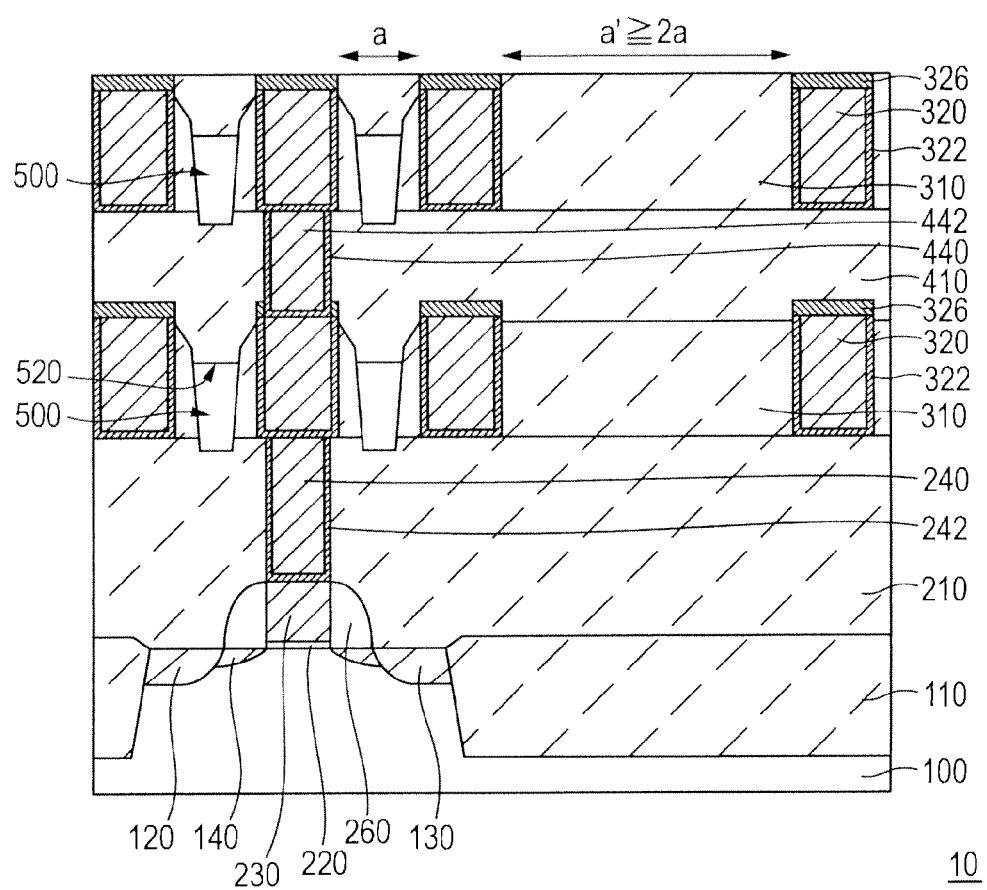
FIG. 17 is a sectional view showing the structure of a semiconductor device according to a sixth embodiment of the invention.

FIG. 17 is a sectional view showing the structure of a semiconductor device 10 according to the sixth embodiment. The sixth embodiment is the same as the first embodiment except that there is a region without an air gap 500 in a plan view. Details are given below.

The left pair of wirings 320 shown in FIG. 17 are first wirings. The distance between the first wirings as a pair is expressed as a. On the other hand, the distance between the right pair of wirings 320 is larger than a.

As shown in FIG. 17, the first interlayer insulating layer 310 has a region in which no air gap is made between wirings 320. In this example, there is no air gap between the left pair of wirings 320. The shape of an air gap 500 may vary depending on the distance between wirings 320, etc. Therefore, there is a possibility that the inter-wiring capacitance may vary depending on the distance between wirings 320. As a solution, in the sixth embodiment, a region in which no air gap 500 is made is provided as desired in order to prevent variation in inter-wiring capacitance.

Distance a' between the wirings 320 in the region without an air gap 500 is, for example, not less than twice the distance a between first wirings. If distance a' between wirings 320 is not less than twice the distance a between first wirings and an air gap 500 is made there, the air gap 500 would be buried in the second interlayer insulating layer 410 and the shape of the air gap 500 would tend to be irregular. Therefore, when no air gap 500 is made between wirings 320 whose distance is not less than twice the distance a between first wirings, the inter-wiring capacitance can be controlled stably.

The method of manufacturing the semiconductor device 10 according to the sixth embodiment is the same as in the first embodiment except a step prior to the first trench formation step. The initial steps prior to the first trench formation step are carried out in the same way as in the first embodiment to form wirings 320 in the first interlayer insulating layer 310 as in the first embodiment.

Next, a photoresist layer (not shown) is formed in a region in which an air gap is not to be made. Then, the first trench formation step is carried out using the photoresist layer as a mask. Then, after the second trench formation step, the photoresist layer is removed by ashing. After that, a second interlayer insulating layer 410 is formed and as a consequence, air gaps 500 are made only in desired regions.

The sixth embodiment brings about the same advantageous effect as the first embodiment. In the sixth embodiment, the first interlayer insulating layer 310 has a region in which there is no air gap 500 between wirings 320. This contributes to prevention of variation in inter-wiring capacitance.

An example of the sixth embodiment has been explained above in which regions with different inter-wiring distances are provided in different places in a plan view and an air gap 500 is made in one region and no air gap 500 is made in another region. As another example, if the inter-wiring distance differs from one wiring layer to another, air gaps 500 may be selectively made in each layer depending on the inter-wiring distance in the layer. For example, a multilayer wiring structure may be formed in which air gaps 500 are made in a lower wiring layer with distance a between first wirings of 40 nm or less as the minimum inter-wiring distance and no air gaps 500 are made in an upper wiring layer with distance a between first wirings of 40 nm or more as the minimum inter-wiring distance. The wiring layer in which air gaps 500 are made may have a multilayer wiring structure as a combination of some of the above other embodiments.

The preferred embodiments have been explained above on the assumption that the first trench formation step and second trench formation step are independent of each other. However, if the first trench formation step and second trench formation step are carried out consistently in a vacuum condition, the two steps may be taken as a series of steps. If that is the case, the first trench 350 and then the second trench 360 may be formed while the conditions are changed gradually.

The above embodiments are assumed to use a metal cap layer 326 as a cap layer. Instead, the cap layer may be made of another material which can be used as a mask. For example, the cap layer may be an insulating film such as SiN film or SiC film or metal oxide film. This type of film can also function as an anti-diffusion film.

So far the preferred embodiments of the present invention have been described referring to the accompanying drawings, but they are just for illustrative purposes and the invention may be embodied in various forms other than the above-mentioned forms.

What is claimed is:

1. A semiconductor device comprising:
   a first interlayer insulating layer comprising a first side face and a second side face;
   a plurality of wirings provided in the first interlayer insulating layer;
   an air gap made between at least one pair of the wirings in the first interlayer insulating layer; and
   a second interlayer insulating layer provided over the wirings and the first interlayer insulating layer with a first bottom face thereof exposed to the air gap,
   wherein the pair of adjacent wirings having a shortest distance there between are first wirings, the first wirings having side faces and upper faces,
   wherein the first side face of the first interlayer insulating layer is in contact with each of the first wirings;
   wherein the second side face of the first interlayer insulating layer is exposed to the air gap and is in contact with a bottom face of the air gap,
   wherein the first side face of the first interlayer insulating layer forms a first angle with one of the side faces of the first wirings, and the second side face of the first interlayer insulating layer forms a second angle with a plane parallel to the one of the side faces of the first wirings, and
   wherein the first angle is larger than the second angle.

2. The semiconductor device according to claim 1, wherein:
   the first interlayer insulating layer has upper ends;
   the upper ends of the first interlayer insulating layer located between the first wirings are in contact with the side faces of the first wirings;
   the first bottom face of the second interlayer insulating layer is below the upper faces of the first wirings; and
   $b/a \leq 0.5$ holds, where a represents distance between the first wirings, and b represents width of a portion of the first interlayer insulating layer which is in contact with the first bottom face of the second interlayer insulating layer.

3. The semiconductor device according to claim 2, wherein $10 \leq c \leq 25$ holds where c represents depth (nm) from a point where the upper end of the first interlayer insulating layer contacts each of the first wirings to a lower end of the first bottom face.

4. The semiconductor device according to claim 2, wherein the air gap is located in a center portion between the pair of wirings from a plan view.

5. The semiconductor device according to claim 2, further comprising a cap layer located over the wiring in a way to overlap the wiring in a plan view and made of a different material from the first interlayer insulating layer.

6. The semiconductor device according to claim 2, wherein the upper end of the first interlayer insulating layer in contact with the wiring is below the upper face of the wiring.

7. The semiconductor device according to claim 2, wherein a bottom face of the air gap is below a bottom face of the wiring.

8. The semiconductor device according to claim 2, wherein the first bottom face is at a level above half of height of the wiring.

9. The semiconductor device according to claim 2, wherein the first interlayer insulating layer has a region in which the air gap is not made between the wirings.

10. The semiconductor device according to claim 9, wherein distance between the wirings in the region in which the air gap is not made is not less than twice as large as distance between the first wirings.

11. The semiconductor device according to claim 2, wherein distance from the side lace of the wiring to the lower end of the first bottom face is not less than 10 nm and not more than 20 nm.

12. The semiconductor device according to claim 2, the first interlayer insulating layer comprising: a first side face in contact with each of the first wirings; and a second side face exposed to the air gap and in contact with a bottom lace of the air gap, wherein an angle between the first side face and the side lace of the first wiring is not less than 20 degrees and not more than 45 degrees.

13. The semiconductor device according to claim 2, the first interlayer insulating layer comprising: a first side face in contact with each of the first wirings; and a second side face exposed to the air gap and in contact with a bottom face of the air gap, wherein an angle between the second side lace and a plane parallel to the side face of the first wiring is not more than 20 degrees.

14. The semiconductor device according to claim 2, further comprising an oxide layer between the pair of wirings and the second interlayer insulating layer.

15. The semiconductor device according to claim 2, wherein the wirings contain Cu.

16. The semiconductor device according to claim 2, further comprising a metal cap layer provided over each of the wirings in a way to overlap the wiring in a plan view,
wherein the metal cap layer contains Ta, TaN, Ti, TiN, Mn, CoWP, CoWB, Co, NiB, W, Al or any one of alloys of these metals.

17. The semiconductor device according to claim 2, wherein the wirings contain Al or W.

18. The semiconductor device according to claim 2, wherein distance between the first wirings is not more than 40 nm.

19. A semiconductor device comprising:
a first interlayer insulating layer having upper ends;
a plurality of wirings provided in the first interlayer insulating layer;
an air gap made between at least one pair of the wirings in the first interlayer insulating layer; and
a second interlayer insulating layer provided over the wirings and the first interlayer insulating layer with a first bottom face thereof exposed to the air gap,
wherein when the pair of adjacent wirings having a shortest distance therebetween are first wirings, the first wirings having side faces and upper faces,
the upper ends of the first interlayer insulating layer located between the first wirings are in contact with the side faces of the first wirings;
the first bottom face of the second interlayer insulating layer is below the upper faces of the first wirings; and
$b/a \leq 0.5$ holds, where a represents distance between the first wirings, and b represents width of a portion of the first interlayer insulating layer which is in contact with the first bottom face of the second interlayer insulating layer,
wherein the first interlayer insulating layer comprises a first side face and a second side face,
wherein the first side face of the first interlayer insulating layer is in contact with each of the first wirings,
wherein the second side face of the first interlayer insulating layer is exposed to the air gap and is in contact with a bottom face of the air gap,
wherein the first side face of the first interlayer insulating layer forms a first angle with one of the side faces of the first wirings, and the second side face of the first interlayer insulating layer forms a second angle with a plane parallel to the one of the side faces of the first wirings, and
wherein the first angle is larger than the second angle.

* * * * *